(12) United States Patent
Litvay et al.

(10) Patent No.: US 7,759,540 B2
(45) Date of Patent: Jul. 20, 2010

(54) ABSORBENT ARTICLES CONTAINING ABSORBENT CORES HAVING ZONED ABSORBENCY AND METHODS OF MAKING SAME

(75) Inventors: John Litvay, Duluth, GA (US); Andrew Baker, Alpharetta, GA (US)

(73) Assignee: Paragon Trade Brands, LLC, Great Neck, NY (US)

( * ) Notice: Subject to any disclaimer, the term of this patent is extended or adjusted under 35 U.S.C. 154(b) by 16 days.

(21) Appl. No.: 10/200,334

(22) Filed: Jul. 23, 2002

(65) Prior Publication Data

US 2004/0019338 A1    Jan. 29, 2004

(51) Int. Cl.
*A61F 13/15* (2006.01)
(52) U.S. Cl. .................. 604/379; 604/380; 604/367; 604/378; 604/368; 604/382; 604/385.01
(58) Field of Classification Search .......... 604/379, 604/380, 367, 378, 368, 382, 385.01; 442/375, 442/381, 393; 428/221
See application file for complete search history.

(56) References Cited

U.S. PATENT DOCUMENTS

| | | | |
|---|---|---|---|
| 2,940,133 A | 6/1960 | Heritage | |
| 3,061,878 A | 11/1962 | Chapman | |
| 3,816,227 A | 6/1974 | Schaar | |
| 4,592,751 A * | 6/1986 | Gegelys | 604/368 |
| 4,699,823 A * | 10/1987 | Kellenberger et al. | 428/219 |
| 4,744,932 A * | 5/1988 | Browne | 264/41 |
| 4,747,166 A * | 5/1988 | Kuntz | 4/144.1 |
| 5,281,207 A | 1/1994 | Chmielewski et al. | |
| 5,350,370 A | 9/1994 | Jackson et al. | |
| 5,425,725 A | 6/1995 | Tanzer et al. | |
| 5,436,066 A | 7/1995 | Chen | |
| 5,466,513 A | 11/1995 | Wanek et al. | |
| H1565 H | 7/1996 | Brodof et al. | |
| 5,681,300 A | 10/1997 | Ahr et al. | |
| 5,849,002 A | 12/1998 | Carlos et al. | |
| 5,853,402 A | 12/1998 | Faulks et al. | |
| 5,863,288 A | 1/1999 | Baker | |
| 5,876,388 A | 3/1999 | McDowall et al. | |
| 5,882,464 A | 3/1999 | Theisgen et al. | |
| 5,891,120 A | 4/1999 | Chmielewski | |
| 5,922,165 A | 7/1999 | Bitowft et al. | |
| 5,983,650 A | 11/1999 | Ando et al. | |
| 6,068,620 A | 5/2000 | Chmielewski | |

FOREIGN PATENT DOCUMENTS

| DE | 1510427 | 10/1970 |
|---|---|---|
| EP | 0958801 A1 | 11/1999 |

* cited by examiner

*Primary Examiner*—Jacqueline F. Stephens
(74) *Attorney, Agent, or Firm*—Amster, Rothstein & Ebenstein LLP

(57) ABSTRACT

The present invention relates generally to an absorbent core for an absorbent article, and more particularly to an absorbent core having zoned absorbency due to specific placement of adhesives or specific lack of adhesive. Such absorbent cores provide the flexibility of creating precise zoning of particular properties throughout the core, and they provide improved comfort and fit.

25 Claims, 8 Drawing Sheets

ABSORBENT ARTICLES CONTAINING ABSORBENT CORES HAVING ZONED ABSORBENCY AND METHODS OF MAKING SAME

FIELD OF THE INVENTION

The present invention relates generally to an absorbent core for an absorbent article, and more particularly to an absorbent core having zoned absorbency due to specific placement of adhesives or specific lack of adhesive. Such absorbent cores provide the flexibility of creating precise zoning of particular properties throughout the core, and they provide improved comfort and fit.

BACKGROUND OF THE INVENTION

Disposable absorbent garments such as infant diapers or training pants, adult incontinence products and other such products typically were constructed with a moisture-impervious outer backing sheet, a moisture-pervious body-contacting inner liner sheet, and a moisture-absorbent core sandwiched between the liner and backing sheets. Much effort has been expended to find cost-effective materials for absorbent cores that display favorable liquid absorbency and retention. Superabsorbent materials in the form of granules, beads, fibers, bits of film, globules, etc., have been favored for such purposes. Such superabsorbent materials generally are polymeric gelling materials that are capable of absorbing and retaining even under moderate pressure large quantities of liquid, such as water and body wastes, relative to their own weight.

The superabsorbent material generally is a water-insoluble but water-swellable polymeric substance capable of absorbing water in an amount which is at least ten times the weight of the substance in its dry form. In one type of superabsorbent material, the particles or fibers may be described chemically as having a back bone of natural or synthetic polymers with hydrophilic groups or polymers containing hydrophilic groups being chemically bonded to the back bone or in intimate admixture therewith. Included in this class of materials are such modified polymers as sodium neutralized cross-linked polyacrylates and polysaccharides including, for example, cellulose and starch and regenerated cellulose which are modified to be carboxylated, phosphonoalkylated, sulphoxylated or phosphorylated, causing the SAP to be highly hydrophilic. Such modified polymers may also be cross-linked to reduce their water-solubility.

The ability of a superabsorbent material to absorb liquid typically is dependent upon the form, position, and/or manner in which particles of the superabsorbent are incorporated into the absorbent core. Whenever a particle of the superabsorbent material and absorbent core is wetted, it swells and forms a gel. Gel formation can block liquid transmission into the interior of the absorbent core, a phenomenon called "gel blocking." Gel blocking prevents liquid from rapidly diffusing or wicking past the "blocking" particles of superabsorbent (e.g., those particles that have swelled and touched an adjacent swelled particle), causing portions of a partially hydrated core to become inaccessible to multiple doses of urine. Further absorption of liquid by the absorbent core must then take place via a diffusion process. This is typically much slower than the rate at which liquid is applied to the core. Gel blocking often leads to leakage from the absorbent article well before all of the absorbent material in the core is fully saturated.

Despite the incidence of gel blocking, superabsorbent materials are commonly incorporated into absorbent cores because they absorb and retain large quantities of liquid, even under load. However, in order for superabsorbent materials to function, the liquid being absorbed in the absorbent structure must be transported to unsaturated superabsorbent material. In other words, the superabsorbent material must be placed in a position to be contacted by liquid. Furthermore, as the superabsorbent material absorbs the liquid it must be allowed to swell. If the superabsorbent material is prevented from swelling, it will cease absorbing liquids.

Adequate absorbency of liquid by the absorbent core at the point of initial liquid contact and rapid distribution of liquid away from this point is necessary to ensure that the absorbent core has sufficient capacity to absorb subsequently deposited liquids. Previously known absorbent cores have thus attempted to absorb quickly and distribute large quantities of liquids throughout the absorbent core while minimizing gel blocking during absorption of multiple doses of liquid.

In general, some of the important performance attributes of an absorbent core of a diaper (or any other absorbent garment) are functional capacity, rate of absorption, core stability in use, type of SAP, ratio of fibrous material to SAP, the type and basis weight of glue or tackifying agent used to adhere the SAP to the fibrous material or tissue wrapping, and the basis weight of the core. Absorption under load or AUL is a good measure of functional capacity and the rate at which that absorption occurs. AUL is believed to be a function of both SAP basis weight (mass per unit area) and the composition of SAP used in the composite. Increasing the basis weight decreases the performance/cost ratio of the absorbent core, making them uneconomical. Also, increased basis weights tend to affect the fit and comfort of the garment, as well as impacting the packaging and shipping costs.

It is known to provide absorbent laminates comprised of, for example, an upper and lower layers, and a central fibrous layer containing from 50% to 95% by weight SAP. U.S. Pat. No. 6,068,620, the disclosure of which is incorporated herein by reference in its entirety and in a manner consistent with the present disclosure, discloses that the upper and lower layers are comprised of tissue, airlaid fluff pulp or synthetic nonwoven fibrous layers. The upper and lower layers are said to assist in maintaining the integrity of the core, the laminate layered arrangement is said to minimize gel blocking, and the laminate can be folded in various configurations.

It also is known to provide absorbent cores comprised of differing materials in an attempt to maximize comfort and efficiency of the core, and to provide areas having varying degrees of absorbency. U.S. Pat. No. 5,849,002, the disclosure of which is incorporated by reference herein in its entirety, discloses absorbent cores having three zones: (i) one zone for receiving fluids; (ii) one zone for distributing and storing fluids; and (iii) one zone for preventing leakage. U.S. Pat. No. 5,853,402, the disclosure of which is incorporated by reference herein in its entirety, discloses composite absorbent cores comprising at least an absorbent material and a porous resilient material. Other composite, zoned, or multi-component cores are disclosed in, for example, U.S. Pat. Nos. 5,681,300 (blended absorbent core), 5,882,464 (crimping to join two absorbent structures), 5,891,120 (varying SAP concentration throughout core), 5,425,725 and 5,983,650 (multiple fiber free SAP pockets in core), and 5,922,165 (method of joining outer layers with absorbent core disposed between the outer layers). The respective disclosures of each of these documents are incorporated by reference herein in their entirety.

SUMMARY OF THE INVENTION

It would be desirable to provide an absorbent garment having an improved ability to retain fluids and consequently, to prevent leakage. It also would be desirable to provide an absorbent core that includes an increased amount of superabsorbent polymers, but at the same time does not suffer from gel blocking to an appreciable extent. A further desirable feature would be to provide an absorbent core having varying areas of absorbency to account for variations in gender and age, that is relatively easy and inexpensive to manufacture. An additional desirable feature would be to provide an absorbent core having increased amounts of superabsorbent polymers optionally dispersed within in a fibrous matrix whereby the polymers generally are free to move about the core due to gravity and other forces, but which do not spill out from the core to any appreciable extent during manufacture or use.

It is therefore a feature of an embodiment of the invention to provide an absorbent garment having an improved ability to retain fluids, especially in areas of the core where fluid retention is needed most. It is an additional feature of an embodiment of the invention to provide an absorbent garment that includes an absorbent core having SAP particles as a substantial percentage of its basis weight, but at the same time reducing gel blocking, i.e., retaining high SAP efficiency. An additional feature of the invention is to provide an absorbent article having specific desired properties in select areas of the absorbent core that is relatively inexpensive to manufacture, that provides the improved properties above, and that is comfortable to wear.

These and other features of the invention can be achieved by an absorbent article including a top sheet, a back sheet and an absorbent laminate core disposed between the top sheet and the back sheet. The absorbent laminate core of the invention preferably is comprised of an upper layer, a lower layer, and a central absorbent layer including a mixture of tow fibers and SAP disposed between the upper and lower layer. The absorbent laminate core of the invention contains areas of varying absorbency due to the varying concentrations of SAP in the laminate core.

In accordance with a feature of an embodiment of the invention, the absorbent laminate core has adhesives applied only in the lateral edges to seal the edges and prevent SAP from falling out of the laminate core when folding. This absorbent core therefore can be folded in any number of configurations to allow for lesser or greater amounts of absorbent material in select regions. In an alternative and preferred embodiment of the invention, the absorbent laminate core optionally has adhesive applied only in the lateral edges, and the lateral edges are crimped to thereby prevent SAP from falling out of the laminate core during manufacture and use.

In accordance with another feature of an embodiment of the invention, the absorbent laminate core has adhesives applied in select regions where more absorbency is needed (e.g., male and/or female insult point, etc.). In another feature of an embodiment of the invention, no adhesive is applied when making the absorbent laminate core. In this embodiment, the SAP will settle by gravity to the lowest points in the core, thereby providing selective regions of absorbency throughout the core.

In accordance with an additional feature of an embodiment of the invention, there is provided a method of making an absorbent article that includes providing a top sheet material and a back sheet material. The method also include preparing an absorbent laminate core that includes providing an upper layer and a lower layer and disposing between the upper and lower layers, a central absorbent layer including a mixture of tow fibers and SAP. The absorbent laminate core then is disposed between the top sheet material and the back sheet material. Preparing the absorbent laminate core includes supplying select regions of adhesive to at least one of the upper and lower layers prior to disposing the central absorbent layer there between, to thereby provide an absorbent laminate core having select regions of absorbency due to the presence of varying concentrations of SAP. In one embodiment of the invention, no adhesive is applied to the upper or lower layer thereby providing a gravitationally zoned absorbent laminate core.

These and other features and advantages of the preferred embodiments will become more readily apparent when the detailed description of the preferred embodiments is read in conjunction with the attached drawings.

DETAILED DESCRIPTION OF THE PREFERRED EMBODIMENTS

Figure 1:
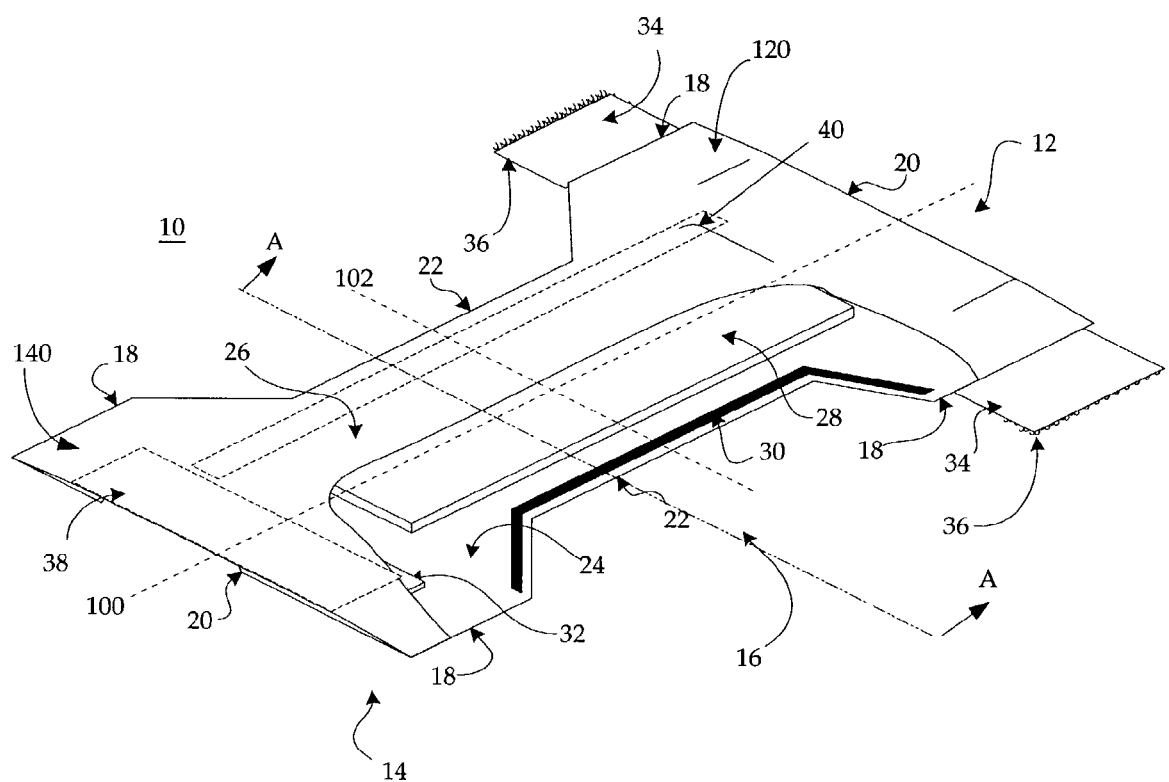
FIG. 1 is a partially cut-away view of an embodiment of the present invention, shown with elastic members fully stretched in the main portion of the garment.

As used herein, the terms "absorbent garment," "absorbent article" or simply "article" or "garment" refer to devices that absorb and contain body fluids and other body exudates. More specifically, these terms refer to garments that are placed against or in proximity to the body of a wearer to absorb and contain the various exudates discharged from the body. A non-exhaustive list of examples of absorbent garments includes diapers, diaper covers, disposable diapers, training pants, feminine hygiene products and adult incontinence products. Such garments may be intended to be discarded or partially discarded after a single use ("disposable" garments). Such garments may comprise essentially a single inseparable structure ("unitary" garments), or they may comprise replaceable inserts or other interchangeable parts.

The present invention may be used with all of the foregoing classes of absorbent garments, without limitation, whether disposable or otherwise. The embodiments described herein provide, as an exemplary structure, a diaper for an infant, however this is not intended to limit the claimed invention. The invention will be understood to encompass, without limitation, all classes and types of absorbent garments, including those described herein. Preferably, the absorbent core is thin in order to improve the comfort and appearance of a garment.

Throughout this description, the expressions "upper layer," "lower layer," "above" and "below," which refer to the various components included in the absorbent core units of the invention (including the layers surrounding the absorbent core units) are used merely to describe the spatial relationship between the respective components. The upper layer or component "above" the other component need not always remain vertically above the core or component, and the lower layer or component "below" the other component need not always remain vertically below the core or component. Indeed, embodiments of the invention include various configurations whereby the core is folded in such a manner that the upper layer ultimately becomes the vertically highest and vertically lowest layer at the same time. Other configurations are contemplated within the context of the present invention.

The term "component" can refer, but is not limited, to designated selected regions, such as edges, corners, sides or the like; structural members, such as elastic strips, absorbent pads, stretchable layers or panels, layers of material, or the like; or a graphic. The term "graphic" can refer, but is not limited, to any design, pattern, indicia or the like.

Throughout this description, the term "disposed" and the expressions "disposed on," "disposing on," "disposed in," "disposed between" and variations thereof (e.g., a description of the article being "disposed" is interposed between the words "disposed" and "on") are intended to mean that one element can be integral with another element, or that one element can be a separate structure bonded to or placed with or placed near another element. Thus, a component that is "disposed on" an element of the absorbent garment can be formed or applied directly or indirectly to a surface of the element, formed or applied between layers of a multiple layer element, formed or applied to a substrate that is placed with or near the element, formed or applied within a layer of the element or another substrate, or other variations or combinations thereof.

Throughout this description, the terms "top sheet" and "back sheet" denote the relationship of these materials or layers with respect to the absorbent core. It is understood that additional layers may be present between the absorbent core and the top sheet and back sheet, and that additional layers and other materials may be present on the side opposite the absorbent core from either the top sheet or the back sheet.

Throughout this description, the expression "tow fibers" relates in general to any continuous fiber. Tow fibers typically are used in the manufacture of staple fibers, and preferably are comprised of synthetic thermoplastic polymers. Usually, numerous filaments are produced by melt extrusion of the molten polymer through a multi-orifice spinneret during manufacture of staple fibers from synthetic thermoplastic polymers in order that reasonably high productivity may be achieved. The groups of filaments from a plurality of spinnerets typically are combined into a tow which is then subjected to a drawing operation to impart the desired physical properties to the filaments comprising the tow. Tow as used in the context of the present invention also encompasses modified tow fibers that have been either surface or internally modified (chemically or otherwise) to improve various desired properties of the fibers (e.g., wicking, etc.).

The present invention relates generally to absorbent articles, and in particular to an absorbent article that contains a top sheet, a back sheet, and an absorbent laminate core disposed between the top sheet and the back sheet. The absorbent laminate core of the invention preferably has varying concentrations of SAP throughout its cross-section, whereby the central absorbent layer is comprised of a mixture of tow fibers and SAP.

The invention also relates in general to a method of making an absorbent article that includes providing a top sheet material and a back sheet material. The method also includes preparing an absorbent laminate core that contains an upper layer, a lower layer, and at least a central absorbent layer comprised of a mixture of tow fibers and SAP disposed between the upper and lower layers. Preparing the absorbent laminate core includes supplying select regions of adhesive to at least one of the upper and lower layers prior to disposing the central absorbent layer there between, to thereby provide an absorbent laminate core having select regions of absorbency due to the presence of varying concentrations of SAP. In one embodiment of the invention, no adhesive is applied to the upper or lower layer thereby providing a gravitationally zoned absorbent laminate core.

The absorbent article of the invention preferably has a front waist region, a rear waist region and a crotch region positioned between the front and rear waist regions. The front waist region and rear waist region can be associated with one another to form a waist opening, and two leg openings. Those skilled in the art recognize that "front" and "rear" in the context of the invention denote for clarity purposes only the front and rear of a user, and that the absorbent article could be reversed whereby the previously described "front" portion becomes the rear portion, and vice versa.

Leg elastics preferably are provided along the leg openings for securely holding the leg openings against the thighs of the wearer to improve containment and fit. A fastening system, either resealable or permanent, preferably holds the absorbent article around the wearer's waist. The fastening system assists in associating the front waist region with the rear waist region. A pair of stand-up leg gathers or waist containment flaps may be attached to or formed from the body's side surface of the top sheet.

The preferred embodiments of the absorbent article of the invention include an absorbent laminate core comprising a mixture of tow fibers and SAP. The absorbent laminate core has select regions of absorbency due to the presence or absence of select regions of adhesives. The absorbent laminate core and/or the absorbent article also may include one or more additional components, such as at least one layer selected from an acquisition layer, a distribution layer, an additional fibrous layer containing SAP, a wicking layer, a storage layer, or combinations and fragments of these layers.

Other non-SAP-containing roll good materials such as latex or thermally bonded airlaid fluff pulp, (e.g., roll good available from Walkisoft, Merfin or Fort James), or synthetic spunbonded, carded, or hydro-entangled non-woven may be positioned above and below the absorbent core. The absorbent laminate core also may be comprised of more than one absorbent core unit. The absorbent laminate core of the invention preferably contains 50-95% by weight particulate or fibrous SAP and a tow fiber, which preferably is capable of maintaining high SAP efficiency. As described in U.S. Pat. No. 6,068,620, SAP efficiency can be expressed as the ratio of the actual SAP absorbency under load, or AUL (expressed as grams of saline absorbed per gram of SAP in the laminate), and the maximum SAP AUL obtained under ideal conditions of low basis weight where gel blocking does not occur. SAP concentrations of 50-95% provide thinner roll good composites for efficient shaping and handling. High SAP concentrations also provide thinner absorbent cores that can provide new options for product design. The absorbent laminate core useful in the invention can be made using either a wet or dry process.

The outer layers of the absorbent laminate cores of the invention typically are designed for optimal wet/dry strength, liquid acquisition and distribution, as well as SAP containment. The inner layers of absorbent cores generally are designed for optimal absorbency and SAP efficiency. Designers of absorbent cores in the past have had to combine the attributes of the outer and inner layers into a homogeneous composite, often leading to an unacceptable compromise.

Absorbent cores made of tow fibers and SAP typically include a tackifying agent or other type of material to adhere the SAP to the fibers, or to contain the SAP. Use of tackifying agents and/or adhesives to adhere the SAP to the fibers, however, can have an adverse effect on the absorbency properties of the SAP, and can cause excessive gel blocking. Traditional cores also make it difficult to vary the absorbency throughout the cross-section of the absorbent laminate core. These conventional cores typically were designed with a single basis weight, a single type of SAP, a single ratio of fiber tow to SAP, a single glue basis weight, and a single glue type. Using different types of glue, SAP, or fiber during manufacture of the core was not previously thought to have been practical. In addition, varying any of these parameters throughout the length and/or width of the absorbent core is not practical from a manufacturing standpoint.

The present invention is premised in part on the discovery that varying amounts of SAP can be provided throughout the cross-section of the absorbent laminate core by providing adhesives only in select regions on the upper and/or lower layers of the absorbent laminate core (or no adhesives in one preferred embodiment). By providing adhesives in select regions of the upper and/or lower layers, more SAP will adhere to the upper and/or lower layers in the areas where the adhesives are present, thereby providing enhanced absorbency in those areas. In addition, providing the adhesives to the upper and/or lower layers is easier and less problematic from a manufacturing perspective than spraying adhesives onto the fibers and SAP during manufacture of the central layer. Applying the adhesive in this manner also is not believed to significantly coat the SAP particles entirely, which in turn does not adversely affect the absorbency properties of the SAP as much as it would were the adhesive applied during formation of the central absorbent layer. The adhesives can be provided in such a manner by select positioning of adhesive spray nozzles, by controlling the timing of the spray nozzle activation, and by other methods recognized by those having ordinary skill in the art.

The invention now will be described with reference to the attached drawings illustrating preferred embodiments of the invention. For clarity, features that appear in more than one Figure have the same reference number in each Figure.

FIG. 1 is a partially cut away depiction of an exemplary embodiment of an absorbent garment 10 (preferably a disposable absorbent garment) of the present invention. The embodiment shown in FIG. 1 is an infant's diaper, however, this depiction is not intended to limit the invention, and those skilled in the art appreciate that the invention covers other types of absorbent articles. For simplicity, however, the invention will be described with reference to an infant's diaper. The garment 10 of FIG. 1 is depicted in a generally flattened position, with the body-facing side facing down, and with the various elastic components depicted in their relaxed condition with the effects of the elastics removed for clarity (when relaxed, the elastics typically cause the surrounding material to gather or "shirr"). In the flattened position, the garment 10 may have a generally hourglass shaped structure, but it may also have any other shape suitable for the given application, such as a rectangular shape, a trapezoidal shape, a "T" shape, and the like.

As used herein, the longitudinal axis 100 of the garment is the dimension of the garment corresponding to the front-to-rear dimension of the user, and the lateral axis 102 of the garment is the dimension corresponding to the side-to-side dimension of the user.

In use, the invention comprises a pant-like garment 10 having a waist-encircling region and a crotch region. The waist-encircling region may comprise a first waist region 12, disposed adjacent to, for example, the back waist region of a wearer's body, and a second waist region 14, disposed adjacent to, for example, the front waist region of a wearer's body. The first and second waist regions 12, 14, may correspond to the front and back of the wearer's body, respectively, depending on whether garment 10 is attached in front of or behind the subject wearer. The first and second waist regions are joined together at or near their lateral edges 18, causing the longitudinally distal edges 20 of the garment 10 to form the perimeter of a waist opening. A crotch region 16 extends between the first and second waist regions 12, 14, and the crotch edges 22 form the perimeter of a pair of leg openings, when the garment 10 is placed on a subject wearer.

The garment 10 preferably comprises a top sheet 24, and a back sheet 26, which may be substantially coterminous with the top sheet 24. When the garment 10 is being worn, the top sheet 24 faces the wearer's body, and the back sheet 26 faces away from the wearer. An absorbent laminate core 28 preferably is disposed between at least a portion of the top sheet 24 the back sheet 26.

An embodiment of the present invention may further comprise various additional features. One or more pairs of elastic gathers 30 may extend adjacent the crotch edges 22. The garment 10 may also comprise one or more waste containment systems, such as inboard standing leg gathers 40, which preferably extend from the second waist region 14 to the first waist region 12 along opposite sides of longitudinal center line 100 (only one standing leg gather system 40 is shown in FIG. 1 for purposes of clarity). One or both of the first and second waist regions 12, 14 may also be equipped with strips of elastic waist foam 32 or other elastically extensible material, which help contract the garment around the wearer's waist, providing improved fit and leakage prevention.

The absorbent garment 10 also preferably includes fastening elements to enable attachment of the first waist region 12 to second waist region 14. Fastening elements preferably include a pair of tabs 34 that extend laterally away from opposite lateral edges 18 of the first waist region 12 of the garment 10. The tabs 34 may comprise an elastically extensible material (not shown), and may be designed to stretch around a wearer's waist to provide improved fit, comfort, and leakage protection. Such elasticized tabs 34 may be used in conjunction with, or in lieu of, waist foam 32, or other elastically extensible materials 32.

At least one fastening mechanism 36 (collectively referred to as "fastener 36") is attached to each tab 34 for attaching the tab to the second waist region 14, thereby providing the garment 10 with a pant-like shape, and enabling garment 10 to be fixed or otherwise fitted on the wearer. The fasteners 36 may attach to one or more target devices 38 located in the second waist region 14.

Although not shown in the drawings, the absorbent garment 10 may also include grips attached along one of its edges proximal to each tab 34 to enable a caregiver to pull the grips, and not on the ends of the tabs 34, around the wearer and over the target devices 38 to thereby secure the fasteners 36 to the one or more target devices 38.

The various parts of the garment 10 can be attached to one another or associated with one another to form a structure that preferably maintains its shape during the useful life of the garment 10. As used herein, the terms "attached," "joined," "associated," and similar terms encompass configurations whereby a first part is directly joined to a second part by affixing the first part directly to the second part, by indirectly joining the first part to the second part through intermediate members, and by fixing the relative positions of various parts by capturing parts between other parts. Those skilled in the art will appreciate that various methods or combinations of methods may be used to securely join the respective parts of the garment 10 to one another.

The top sheet 24 and back sheet 26 may be constructed from a wide variety of materials known in the art. The invention is not intended to be limited to any specific materials for these components. The top sheet 24 and back sheet can be shaped and sized according to the requirements of each of the various types of absorbent garment, or to accommodate various user sizes. In an embodiment of the invention in which the garment 10 is a diaper or an adult incontinence brief, the combination of top sheet 24 and back sheet 26, may have an hourglass shape, as seen in FIG. 1, or may have a rectangular, trapezoidal, "T" shape, or other shape.

Due to the wide variety of backing and liner sheet construction and materials currently available, the invention is not intended to be limited to any specific materials or constructions of these components. The back sheet 26 preferably is made from any suitable pliable liquid-impervious material known in the art. Typical back sheet materials include films of polyethylene, polypropylene, polyester, nylon, and polyvinyl chloride and blends of these materials. For example, the back sheet can be made of a polyethylene film having a thickness in the range of 0.02-0.04 mm. The back sheet 26 may be pigmented with, for example, titanium dioxide, to provide the garment 10 with a pleasing color or to render the back sheet 26 opaque enough that exudates being contained by the garment 10 are not visible from outside the garment. In addition, the back sheet 26 may be formed in such a manner that it is opaque, for example, by using various inert components in the polymeric film and then biaxially stretching the film. Other back sheet materials will be readily apparent to those skilled in the art. The back sheet 26 preferably has sufficient liquid imperviousness to prevent any leakage of fluids. The required level of liquid imperviousness may vary between different locations on the garment 10.

The back sheet 26 may further comprise separate regions having different properties. In a preferred embodiment, portions of the back sheet 26 are air-permeable to improve the breathability, and therefore comfort, of the garment 10. The different regions may be formed by making the back sheet 26 a composite of different sheet materials, chemical treatment, heat treatment, or other processes or methods known in the art. Some regions of the back sheet 26 may be fluid pervious. In one embodiment of the invention, the back sheet 26 is fluid impervious in the crotch 16, but is fluid pervious in portions of the first and second waist regions 12, 14. The back sheet 26 may also be made from a laminate of overlaid sheets of material.

The moisture-pervious top sheet 24 can be comprised of any suitable relatively liquid-pervious material known in the art that permits passage of liquid there through. Non-woven liner sheet materials are exemplary because such materials readily allow the passage of liquids to the underlying absorbent laminate core 28. Examples of suitable liner sheet materials include non-woven spun bond or carded webs of polypropylene, polyethylene, nylon, polyester and blends of these materials.

The back sheet 26 may be covered with a fibrous, non woven fabric such as is disclosed, for example, in U.S. Pat. No. 4,646,362 issued to Heran et al., the disclosure of which is hereby incorporated by reference in its entirety and in a manner consistent with this disclosure. Materials for such a fibrous outer liner include a spun-bonded non woven web of synthetic fibers such as polypropylene, polyethylene or polyester fibers; a non woven web of cellulosic fibers, textile fibers such as rayon fibers, cotton and the like, or a blend of cellulosic and textile fibers; a spun-bonded non woven web of synthetic fibers such as polypropylene; polyethylene or polyester fibers mixed with cellulosic, pulp fibers, or textile fibers; or melt blown thermoplastic fibers, such as macro fibers or micro fibers of polypropylene, polyethylene, polyester or other thermoplastic materials or mixtures of such thermoplastic macro fibers or micro fibers with cellulosic, pulp or textile fibers. Alternatively, the back sheet 26 may comprise three panels wherein a central poly back sheet panel is positioned closest to absorbent laminate core 28 while outboard non-woven breathable side back sheet panels are attached to the side edges of the central poly back sheet panel. Alternatively, the back sheet 26 may be formed from microporous poly coverstock for added breathability.

Figure 2:
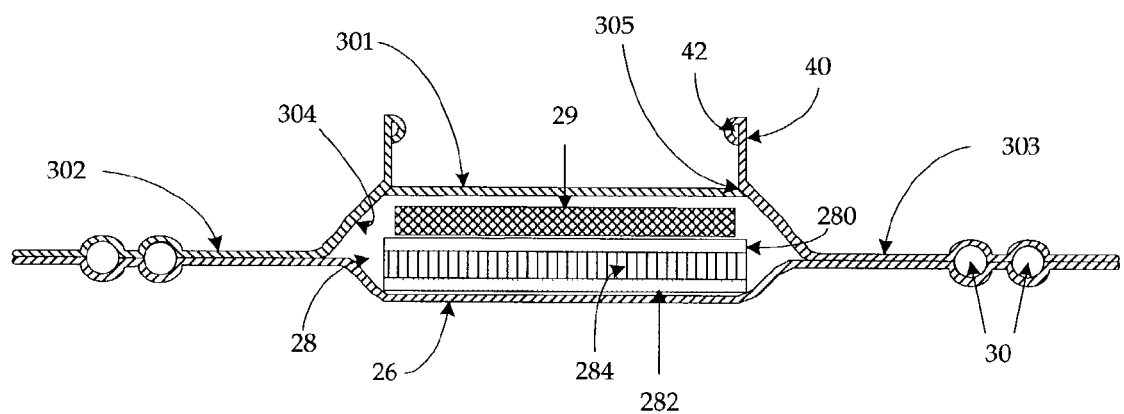
FIG. 2 is a cross-sectional view of the absorbent garment in FIG. 1 taken along line A-A.

As illustrated in more detail in FIG. 2, the top sheet 24 may be formed of three separate portions or panels. Those skilled in the art will recognize, however, that top sheet 24 need not be made of three separate panels, and that it may be comprised of one unitary item. A first top sheet panel 301 may comprise a central top sheet panel formed from preferably a liquid-pervious material that is either hydrophobic or hydrophilic. The central top sheet panel 301 may be made from any number of materials, including synthetic fibers (e.g., polypropylene or polyester fibers), natural fibers (e.g., wood or cellulose), apertured plastic films, reticulated foams and porous foams to name a few. One preferred material for a central top sheet panel 301 is a cover stock of single ply non-woven material which may be made of carded fibers, either adhesively or thermally bonded, perforated plastic film, spun bonded fibers, or water entangled fibers, which generally weigh from 0.3-0.7 oz./sq. yd. and have appropriate and effective machine direction and cross-machine direction strength suitable for use as a baby diaper cover stock material. The central top sheet 301 panel preferably extends from substantially the second waist region 14 to the first waist region 12, or a portion thereof.

The second and third top sheet panels 302, 303 (e.g., outer top sheet panels), in this alternative embodiment may be positioned laterally outside of the central top sheet panel 301. The outer top sheet panels 302, 303 are preferably substantially liquid-impervious and hydrophobic, preferably at least in the crotch area. The outer edges of the outer top sheet panels may substantially follow the corresponding outer perimeter of the back sheet 26. The material for the outer top sheet portions or panels is preferably polypropylene and can be woven, non-woven, spun bonded, carded or the like, depending on the application.

The inner edges 304 (FIG. 2) of the outer top sheet portions or panels 302, 303 preferably are attached by, e.g., an adhesive, to the outer edges 305 of the inner top sheet portion or panel 301. At the point of connection with the outer edges 305 of the inner top sheet portion or panel 301, the inner edges 304 of the outer top sheet portions or panels 302, 303 extend upwardly to form waste containment flaps 40. The waste containment flaps 40 preferably are formed of the same material as the outer top sheet portions or panels 302, 303, as in the embodiment shown. They are preferably an extension of the outer top sheet portions or panels 302, 303.

The waste containment flaps 40 may be treated with a suitable surfactant to modify their hydrophobicity/hydrophilicity as desired, and they may be treated with skin wellness ingredients to reduce skin irritation. Alternatively, the waste containment flaps 40 may be formed as separate elements and then attached to the body side liner. In this alternative embodiment, the central top sheet portion or panel 301 may extend past the connection point with the waste containment flaps 40, and even extend to the periphery of the back sheet 26.

The waste containment flaps 40 preferably include a portion that folds over onto itself to form a small enclosure. At least one, and depending on the size of the enclosure sometimes more than one, elastic member 42 may be secured in the enclosure in a stretched condition. As has been known at least as long the disclosure of Tetsujiro, Japanese Patent document 40-11543, when the flap elastic 42 attempts to assume the relaxed, unstretched condition, the waste containment flaps 40 rise above the surface of the central top sheet portion or panel 301.

The top sheet 24 (as well as top sheet portions 301, 302, 303) may be made of any suitable relatively liquid-pervious material currently known in the art or later discovered that permits passage of a liquid there through. Examples of suitable top sheet materials include non woven spun-bonded or carded webs of polypropylene, polyethylene, nylon, polyester and blends of these materials, perforated, apertured, or reticulated films, and the like. Non woven materials are exemplary because such materials readily allow the passage of liquids to the underlying absorbent laminate core 28. The top sheet 24 preferably comprises a single-ply non woven material that may be made of carded fibers, either adhesively or thermally bonded, spun bonded fibers, or water entangled fibers, which generally weigh from 0.3-0.7 oz./sq. yd. and have appropriate and effective machine direction (longitudinal) and cross-machine (lateral) direction strength suitable for use as a top sheet material for the given application. The present invention is not intended to be limited to any particular material for the top sheet 24, and other top sheet materials will be readily apparent to those skilled in the art.

The top sheet 24 may further comprise several regions having different properties. In one embodiment of the present invention, the laterally distal portions of the top sheet 24, especially those used to make second and third top sheet panels 302, 303, preferably are substantially fluid impervious and hydrophobic, while the remainder of the top sheet 24 (e.g., central top sheet panel 301) is hydrophilic and fluid pervious. Different top sheet properties, such as fluid perviousness and hydrophobicity, may be imparted upon the top sheet 24 by treating the top sheet 24 with adhesives, surfactants, or other chemicals, using a composite of different materials, or by other means. The top sheet 24 may also be made from a laminate of overlaid sheets of material. The top sheet 24 also may be treated in specific areas like the crotch region, with skin wellness ingredients such as aloe, vitamin E, and the like.

As noted elsewhere herein, the top sheet 24 and back sheet 26 may be substantially coterminous, or they may have different shapes and sizes. The particular design of the top sheet 24 and back sheet 26 may be dictated by manufacturing considerations, cost considerations, and performance considerations. Preferably, the top sheet 24 is large enough to completely cover the absorbent laminate core 28, and the back sheet 26 is large enough to prevent leakage from the garment 10. The design of top sheet 24 and back sheet 26 is known in the art, and a skilled artisan will be able to produce an appropriate top sheet 24 and an appropriate back sheet 26 without undue experimentation.

The top sheet 24 and the back sheet 26 may be associated with one another using a variety of methods known in the art. For example, they may be thermally, ultrasonically, or chemically bonded to one another. They also may be joined using lines of hot melt adhesive or mechanical fasteners, such as thread, clips, or staples. In one embodiment, a hydrophilic adhesive, such as Cycloflex as sold by National Starch, a corporation headquartered in Bridgewater, N.J., is used to join the top sheet 24 to the back sheet 26. The particular joining method may be dictated by the types of materials selected for the top sheet 24 and back sheet 26.

As mentioned above, absorbent garment preferably is provided with leg elastics 30 extending through crotch region 16, adjacent crotch edge 22. The absorbent garment of the invention also preferably is provided with waist elastic material 32 optionally in the first and second waist regions, 12, 14, respectively, to enable and assist in stretching around the wearer. The waist elastics 32 may be similar structures or different to impart similar or different elastic characteristics to the first and second waist regions 12, 14 of the garment. In general, the waist elastics may preferably comprise foam strips positioned at the first and second waist regions 12, 14, respectively. Such foam strips preferably are about ½ to about 1½ inches wide and about 3-6 inches long. The foam strips preferably are positioned between the top sheet portions 24 or panels (301, 302, 303) and the back sheet 26. Alternatively, a plurality of elastic strands may be employed as waist elastics rather than foam strips. The foam strips preferably are comprised of polyurethane, but can be any other suitable material that decreases waist band roll over, reduces leakage over the waist ends of the absorbent garment, and generally improve comfort and fit. The first and optional second waist foam strips 32 preferably are stretched 50-150%, preferably 100% more than their unstretched dimension before being adhesively secured between the back sheet 26 and top sheet 24.

Each edge 22 that forms the leg openings preferably is provided with an adjacent leg elastic containment system 30. In the preferred embodiment, three strands of elastic threads (only two strands are shown in FIG. 2 for purposes of clarity) are positioned to extend adjacent to leg openings between the outer top sheet portions or panels 302, 303 and the back sheet 26. Any suitable elastomeric material exhibiting at least an elongation (defined herein as $(L_S-L_R)/L_R$ where $L_S$ is the stretch length of an elastic element and $L_R$ is retracted length, multiplied by 100 to obtain percent elongation) in the range of 5%-350%, preferably in the range of 200%-300%, can be employed for the leg elastics 30. The leg elastics 30 may be attached to the absorbent article 10 in any of several ways which are known in the art. For example, the leg elastics 30 may be ultrasonically bonded, heat/pressure sealed using a variety of bonding patterns, or glued to the garment 10. Various commercially available materials can be used for the leg elastics 30, such as natural rubber, butyl rubber or other synthetic rubber, urethane, elastomeric materials such as LYCRA (DuPont), GLOSPAN (Globe) or SYSTEM 7000 (Fulflex).

The fastening elements, preferably a fastening system 34 (e.g., tab 34) of the preferred embodiment, is attached to the first waist region 12, and it preferably comprises a tape tab or mechanical fasteners 36. However, any fastening mechanism known in the art will be acceptable. Moreover, the fastening system 34 may include a reinforcement patch below the front waist portion so that the diaper may be checked for soiling without compromising the ability to reuse the fastener. Alternatively, other absorbent article fastening systems are also possible, including safety pins, buttons, and snaps.

As stated previously, the invention has been described in connection with a diaper. The invention, however, is not intended to be limited to application only in diapers. Specifically, the absorbent laminate cores of the preferred embodiments may be readily adapted for use in other absorbent garments besides diapers, including, but not limited to, training pants, feminine hygiene products and adult incontinence products.

The underlying structure beneath the top sheet 24 may include, depending on the diaper construction, various combinations of elements, but in each embodiment, it is contemplated that the absorbent garment will preferably include a absorbent laminate core 28. In addition, an additional layer 29 may be disposed between the top sheet 24 and absorbent core 28, as shown in FIG. 2, and/or other additional layers may be disposed between these layers, or between absorbent laminate core 28 and back sheet 26. An additional layer 29 also may be included in the absorbent laminate core 28. The additional layer(s) 29 may include a fluid transfer layer, a fluid handling layer, a storage layer, a wicking layer, a fluid distribution layer, and any other layer(s) known to those having ordinary skill in the art.

Although the absorbent laminate core 28 depicted in FIG. 2 has a substantially rectangular cross-sectional and plan view shape, other shapes may be used, such as a "T" shape or an hourglass shape. The shape of the absorbent laminate core 28 may be selected to provide the greatest absorbency with a reduced amount of material. The absorbent core may be associated with the top sheet 24, back sheet 26, or any other suitable part of the garment 10 by any method known in the art, in order to fix the absorbent laminate core 28 in place. In addition to the respective layers in the absorbent laminate core 28, as will be described in greater detail hereinafter, the overall absorbent laminate core 28 may be enclosed within a tissue wrapping, as disclosed in U.S. Pat. No. 6,068,620, the disclosure of which is incorporated by reference herein in its entirety. Skilled artisans are capable of designing and wrapping a suitable absorbent laminate core 28 of the invention, using the guidelines provided herein.

The absorbent laminate core 28 may extend into either or both of the first and second waist regions 12, 14. The absorbent laminate core 28 of one preferred embodiment of the invention preferably includes at least three (3) layers whereby two of the layers are outer layers, 280, 282, FIG. 2, preferably outer tissue layers 280, 282, and an inner central fibrous layer 284, which preferably contains a mixture of tow fibers and SAP.

Upper and lower layers 280, 282 can be made of any suitable material capable of containing the inner layer(s) of absorbent core 28. Preferably, upper layer 280 is hydrophilic and fluid pervious, and lower layer 282 is hydrophobic and fluid impervious. It is preferred that upper and lower layers 280, 282 be comprised of a material selected from the group consisting of tissue, airlaid fluff pulp and synthetic non-woven materials. More preferably, upper layer 280 and lower layer 282 are comprised of the same tissue-like material. In various embodiments of the invention, upper layer 280 and lower layer 282 are made of different materials. In other embodiments of the invention, upper layer 280 and lower layer 282 are made of the same material and provided separately, or are made from the same single material and folded to include the central fibrous layer 284.

In a preferred embodiment, the central fibrous layer 284 of absorbent laminate core 28 comprises super absorbent polymer distributed within a fibrous structure. Central fibrous layers 284 of this type generally are known in the art, and exemplary absorbent cores are described in U.S. Pat. No. 6,068,620 and U.S. Pat. No. 5,281,207, both issued to Chmielewski, and U.S. Pat. No. 5,863,288, issued to Baker, the disclosures of each of which are herein incorporated by reference in their entirety and in a manner consistent with this disclosure.

Certain fibrous and particulate additives preferably are used as constituent elements of the absorbent laminate core 28 to maintain high SAP efficiencies when the SAP concentration is in the range of about 50-95%, more preferably about 60-90%, and most preferably about 75-85%. Super absorbent polymers of the surface cross-linked variety perform best in these laminates. These additives preferably are constituent elements of the central fibrous layer 284, and they may be added to the additional layer(s) 29.

The fibrous component of the central layer 284 of absorbent laminate core 28 preferably is comprised of tow fiber, and most preferably is a crimped tow of cellulose acetate or polyester. Before making the absorbent laminate core that includes a tow fiber, the tow fiber typically is unwound and opened, and then cut at various lengths to provide a fibrous mass of material. Skilled artisans are aware of techniques available to open tow fibers and form the opened fibers into a fibrous mass.

In addition to the tow material used as the fibrous component in central fibrous layer 284, other fibrous components also may be used. For example, additional tow fibers (different from original tow fiber), or a low-density roll good made in a separate process may be used in central fibrous layer 284. Still further yet, the fibrous component could also be a carded web formed on-line. Optionally, it is advantageous to introduce from about 1-5% of a thermally bondable fiber into the fibrous component of the central fibrous layer 284 for wet strength and core stability in use.

To maintain high SAP concentrations, the concentration of fibrous material in the central layer 284 of the absorbent laminate core 28 of the invention preferably is about 5-50%, more preferably about 10-30%, and most preferably about 15-25%. Most preferably, the central fibrous layer 284 comprises from about 75-85% SAP and from about 15-25% fibrous materials selected from the foregoing group, or the following fibrous components discussed below.

Particulate additives may be added to central fibrous layer 284 in addition to or as a substitute for the foregoing fibrous additives in order to maintain high SAP efficiency. The particulate additives preferably are insoluble, hydrophilic polymers with particle diameters of 100 μm or less. The particulate additives are chosen to impart optimal separation of the SAP particles. Examples of preferred particulate additive materials include, but are not limited to, potato, corn, wheat, and rice starches. Partially cooked or chemically modified (i.e., modifying hydrophobicity. hydrophilicity, softness, and hardness) starches can also be effective. Most preferably, the particulate additives comprise partially cooked corn or wheat starch because in this state, the corn or wheat are rendered larger than uncooked starch and even in the cooked state remain harder than even swollen SAP. In any event, regardless of the particulate additive chosen, one of the many important criteria is to use particulate additives that are hard hydrophilic materials relative to swollen SAP or which are organic or inorganic polymeric materials about 100 microns in diameter. Fibrous and particulate additives can be used together in these absorbent laminates. Examples of SAP/particulate and SAP/fiber/particulate additives include those described in, for example, U.S. Pat. No. 6,068,620.

Any superabsorbent polymer (SAP) now known or later discovered may be used in central fibrous layer 284 so long as it is capable of absorbing liquids. Useful SAP materials are those that generally are water-insoluble but water-swellable polymeric substance capable of absorbing water in an amount that is at least ten times the weight of the substance in its dry form. In one type of SAP, the particles or fibers may be described chemically as having a back bone of natural or synthetic polymers with hydrophilic groups or polymers containing hydrophilic groups being chemically bonded to the back bone or in intimate admixture therewith. Included in this class of materials are such modified polymers as sodium neutralized cross-linked polyacrylates and polysaccharides including, for example, cellulose and starch and regenerated cellulose which are modified to be carboxylated, phosphonoalkylated, sulphoxylated or phosphorylated, causing the SAP to be highly hydrophilic. Such modified polymers may also be cross-linked to reduce their water-solubility.

Examples of suitable SAP are water swellable polymers of water soluble acrylic or vinyl monomers crosslinked with a polyfunctional reactant. Also included are starch modified polyacrylic acids and hydrolyzed polyacrylonitrile and their alkali metal salts. A more detailed recitation of superabsorbent polymers is found in U.S. Pat. No. 4,990,541 to Nielsen, the disclosure of which is incorporated herein by reference in its entirety.

Commercially available SAPs include a starch modified superabsorbent polymer available under the tradename SANWET® from BASF Corporation, Portsmouth, Va. SANWET® is a starch grafted polyacrylate sodium salt. Other commercially available SAPs include a superabsorbent derived from polypropenoic acid, available under the tradename DRYTECH® 520 SUPERABSORBENT POLYMER from The Dow Chemical Company, Midland Mich.; AQUA KEEP manufactured by Seitetsu Kagaku Co., Ltd.; ARASORB manufactured by Arakawa Chemical (U.S.A.) Inc.; ARIDALL 1125 manufactured by Chemdall Corporation; and FAVOR manufactured by Stockhausen Inc.

In accordance with the present invention, the central fibrous layer 284 is advantageously based upon a tow fiber, and preferably, a continuous crimped filament tow. This fiber structure has high structural integrity, and as such, is distinct from a matrix of discontinuous fibers described as fluff, or fluff pulp in the prior art. The high structural integrity enables the production of stronger webs than those formed from discontinuous fibers, which in turn are believed to enable the production of thinner absorbent pads. In addition, the use of such fibers enables the production of ultra low density absorbent cores, when compared to absorbent cores prepared by dispersing SAP particles in fluff.

The tow fiber can be any continuous or discontinuous thermoplastic filament tow fiber that is capable of being opened and used in combination with SAP in an absorbent core. Preferably, cellulose ester tow is used as the fibrous material in central fibrous layer 284. Non-limiting examples of suitable cellulose esters include cellulose acetate, cellulose propionate, cellulose butyrate, cellulose caproate, cellulose caprylate, cellulose stearate, highly acetylated derivatives thereof such as cellulose diacetate, cellulose triacetate and cellulose tricaproate, and mixtures thereof such as cellulose acetate butyrate. A suitable cellulose ester will include some ability to absorb moisture, (but absorptive capacity is not necessarily required), preferably is biodegradable, and is influenced not only by the substituent groups but also by the degree of substitution. The relationship between substituent groups, degree of substitution and biodegradability is discussed in W. G. Glasser et al, BIOTECHNOLOGY PROGRESS, vol. 10, pp. 214-219 (1994), the disclosure of which is incorporated herein by reference in its entirety.

Continuous filament tow useful in the present invention is beneficially moisture-absorbent and biodegradable. Accordingly, cellulose acetate tow is typically preferred for use in the invention. Typically, the denier per fiber (dpf) of the tow fiber will be in the range of about 1 to 9, preferably about 3 to 6, and most preferably about 4. For the same weight product, filaments of lower dpf may provide increased surface area and increased moisture absorption. Total denier may vary within the range of about 20,000 to 60,000, more preferably from about 25,000 to about 50,000, and most preferably from about 30,000 to about 40,000, depending upon the process used.

It is particularly preferred in the invention to use tow having crimped filaments. Tow materials having crimped filaments are typically easier to open. Separation of filaments resulting from bloom advantageously results in increased available filament surface area for superabsorbent material immobilization and increased moisture absorption. Gel blocking also may be reduced by using crimped tow in the central fibrous layer 284. As therefore may be understood, more crimp is typically better, with in excess of about 20 crimps per inch being usually preferred. Continuous filament, cellulose ester tow having crimped filaments with about 25 to 40 crimps per inch, is commercially available from Hoechst Celanese Corporation, Charlotte, N.C.

It is preferred in the present invention that the tow fibers in central fibrous layer 284 have an average length generally about the same length as the absorbent core. Typically, the two is a continuous filament that is cut to length during manufacture of the core. The average diameter of the tow fibers typically is expressed as the cross sectional area of the fibers, although the width of the fibers preferably is within the range of from about 50 to about 200 mm, more preferably from about 75 to about 150 mm, and most preferably from about 85 to about 120 mm. The cross sectional area is based on the denier and density of the fibers. For example, the denier per foot (dpf) and density (typically an acetate polymer density is about 1.32 g/cm$^3$), can be used to calculate the cross sectional area. A 3.0 dpf acetate polymer fiber has a cross sectional area $2.525 \times 10^{-6}$ cm$^2$.

It is preferred in the invention to use relatively coarse fibers having a low basis weight such that the pore size of the matrix formed by the mass of tow fibers does not entrain some or most of the SAP, but rather allows the SAP to fall freely through the matrix. The basis weight of preferred fibers used in the present invention ranges from about 20 to about 200 g/m$^2$, more preferably from about 50 to about 100 g/m$^2$, and most preferably from about 70 to about 80 g/m$^2$.

If desired, a superabsorbent, absorptive pad of multiple layer thickness, may be provided. To this end, the tow may be, for example, lapped or crosslapped in accordance with conventional procedures. In this way, a superabsorbent, absorptive material of a desired weight and/or thickness may be provided. The specific weight or thickness will depend upon factors including the particular end use. It is especially preferred that the crimped cellulose acetate tow material be opened and then mixed with the SAP particles to form the central fibrous layer 284.

The SAP may be provided in any particle size, and suitable particle sizes vary greatly depending on the ultimate properties desired. Preferably, a fine particulate rather than a coarse particulate, is used in the invention, and preferably a fine particulate that passes through an about 200 mesh screen is used.

It has been known to prepare absorbent cores comprised of cellulose acetate tow or other polymeric fibers and SAP, as described in H1565, and U.S. Pat. Nos. 5,436,066, and 5,350,370, the disclosures of each of which are incorporated by reference herein in its entirety. It was conventional to add tackifying agents, specific size fibers, or specific fibers in combination with fluff, in order to prepare the absorbent core and immobilize the SAP particles. By adding these components during mixing of the fibrous material and SAP, it is difficult to control the concentration of either fiber or SAP across the cross-sectional area of the absorbent laminate core 28. The present invention provides this flexibility by varying the location and amount of adhesive applied to either the upper layer 280, lower layer 282, or both, which in turn affects the distribution of fiber and SAP throughout the cross-sectional area of the absorbent laminate core 28.

The total basis weights of the absorbent laminate core 28 including fibrous materials, SAP, tissue, additional layers, and additives, are anywhere from about 10-600 grams per square meter, preferably from about 25 to about 350 grams per square meter. The most preferred total basis weight of the absorbent laminate core 28 is from about 50 to about 350 grams per square meter. In this regard, the absorbent laminate core of the invention may not include any SAP, but rather may be include only tow fibers and perhaps other absorbent materials. These types of materials can be used as "swimmers," or absorbent articles that can be used by children or adults in the water.

Optionally, about 1-10%, preferably about 5%, by weight of thermally bondable synthetic fibers can be added to the absorbent laminate core 28 to impart additional wet strength to the laminate. This will improve the stability of the core during use of the diaper. The preferred synthetic fibers are polyolefin/polyester fibers and polyester/polyester bicomponent fibers.

Depending on whether a wet or dry process is used to make the absorbent laminate core 28, bonding central fibrous layer 284 with any additional layer(s) 29, and tissue layers 280, 282, can be achieved with hydrogen or adhesive bonds. If the material used to form the absorbent laminate core 28 contains about 1-5% by weight thermally bondable synthetic fibers, bonding can be achieved with thermal bonds.

One of the features of the invention is that absorbent laminate core 28 be made by providing adhesives to either upper or lower layer 280, 282, or both, in varying amounts and in varying locations. The adhesive applicator can be controlled such that the precise location and amount of adhesive applied to either upper or lower layer 280, 282, or both can be varied during a manufacturing run. Accordingly, absorbent garments can be made having varying zones of absorbency without having to shut down the operation. For example, the amount and location of the adhesive 295 (FIGS. 3-6) can be located for optimum absorbency at or about the male insult point (e.g., about 10 cm from the bottom fold in a Stage 4 diaper) for a series of garments, and then changed for optimum absorbency at or about the female insult point (e.g., about 5 cm from the bottom fold in a Stage 4 diaper). Skilled artisans know where the male and female insult points are for the various stages of absorbent garment. Using the guidelines provided herein, a person skilled in the art therefore can design an adhesive application system to selectively apply adhesives to upper and lower layers 280, 282, or both, to provide absorbency zones for a variety of different types of garments (e.g., males, females, young, old, overnight, etc.).

Figure 3:
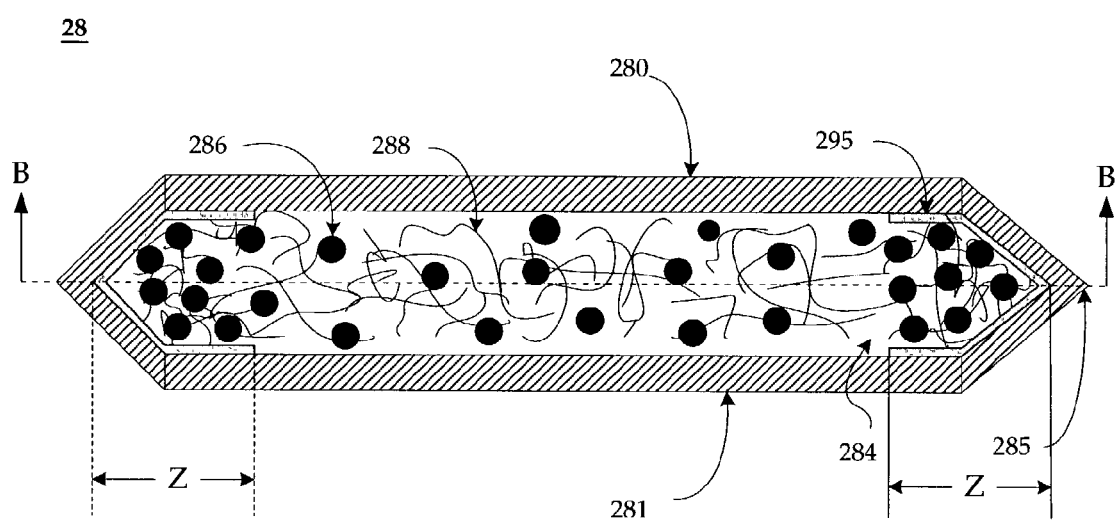
FIG. 3 is a cross-sectional view of an absorbent laminate core in accordance with one embodiment of the invention.
Figure 4:
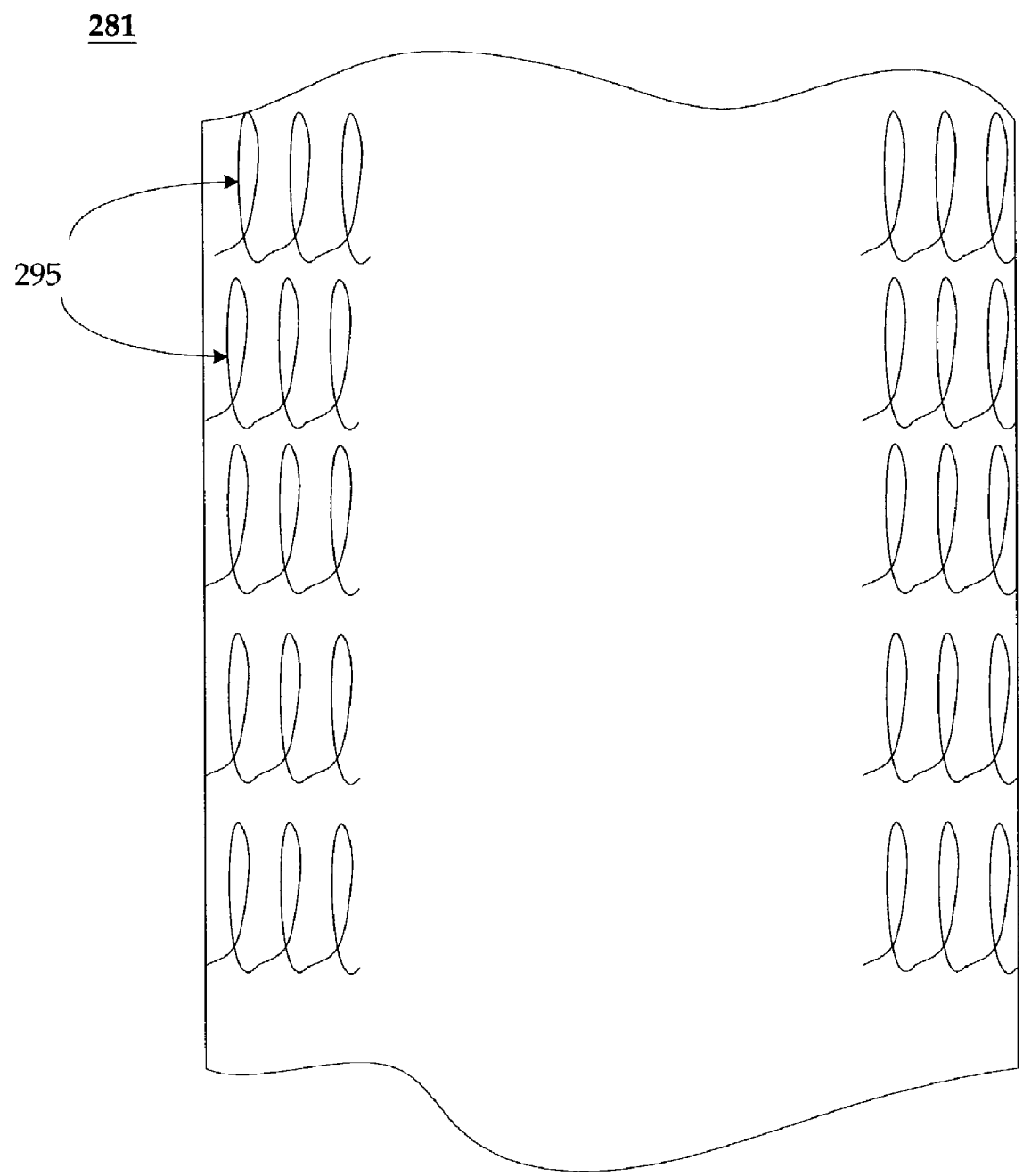
FIG. 4 is a top view of the absorbent laminate core of FIG. 3 taken along line B-B.

FIGS. 3 and 4 illustrate one embodiment of the invention whereby adhesive 295 is applied to either the upper or lower layers 280, 282, or both at or near the lateral edges thereof (adhesive 295 is shown in FIG. 3 as being applied to both upper layer 280 and lower layer 282, although this is not required in the invention). Applying the adhesive 295 to this particular region of the garment will facilitate a better side seal or crimp 285, which can be made even more secure by passing the absorbent laminate core 28 over crimp or bumped rollers during its manufacture.

The central fibrous layer 284 of absorbent laminate core 28 in FIG. 3 is comprised of, inter alia, tow fibers 288, and SAP 286. The adhesive 295 causes more tow fibers 288 and SAP 286 to adhere in the regions where the adhesive 295 is applied. This results in regions or zones "Z" having enhanced absorbency. An absorbent laminate core 28 having enhanced absorbency at its lateral edges, as shown in FIG. 3, would be useful, for example, as a secondary absorbent structure in an absorbent garment 10, whereby the primary absorbent structure would be laterally disposed near the center of absorbent laminate core 28 of FIG. 3 (either above or below it), and could comprise a more efficient SAP material, and materials having greater wicking capabilities. Thus, the primary absorbent structure could handle the initial insult, but then would transfer or "wick" the liquid to the lateral outer portions of the absorbent laminate core 28, where it would be absorbed quickly by the excess fibers 288 and SAP 286.

The embodiment illustrated in FIG. 3 also is beneficial insofar as it prevents loose SAP material 286 from falling out of absorbent laminate core 28. This is especially useful for various embodiments contemplating folding the absorbent laminate core 28. When absorbent laminate cores not containing adhesive at its lateral edges are cut and folded, it is believed that large amounts of mobile SAP material 286 will come out of the core where the pad cut was made. In addition, significant forces are applied to absorbent laminate cores 28 when they are folded at high line speeds. These forces can cause the otherwise mobile SAP material 286 to move around, and to fall out at the edges. Applying adhesives 295 as shown in FIG. 3 will prevent these problems.

The upper and lower layer 289, 282, encase the opened tow and SAP composite, and preferably form the upper and lower tissue layers of the completed garment, but may also form the top sheet and back sheet of the absorbent garment, or any other layers. The upper and lower layers 280, 282, preferably are wider than the central absorbent layer 284 that forms the absorbent core, and their side portions preferably are sealed to one another by bonding, by crimping or by both to prevent release of opened tow and particles of SAP. The absorbent laminate core 28, comprising the assembly of the upper and lower layers 280, 282 and the central absorbent layer 284 including the opened tow and SAP, may be further processed as it is conveyed through the assembly line for inclusion into absorbent garments. For example, the absorbent laminate core 29 may be severed into individual absorbent cores, and the severed ends may be crimped or bonded or both to prevent the SAP from exiting the ends.

Crimping, bonding or both can be performed on the absorbent laminate core 28 of the invention using conventional means. For example, the lateral side edges, and longitudinal edges can be sealed together by intermittent or continuous application of adhesive to the respective portions of the upper and lower layers 280, 282 using any device capable of applying adhesives to a continuous moving web of material. The lateral and/or longitudinal edges then can be pressed together to form a seal. The seal also can be formed ultrasonically, or the respective edges (lateral and/or longitudinal) can be crimped using crimping rollers or any other crimping device known to those having ordinary skill in the art. Using the guidelines provided herein, those skilled in the art will be capable of sealing the lateral and/or longitudinal edges of absorbent laminate core 28 using bonding, crimping, or both.

FIG. 4 is a top view of either upper layer or lower layer 280, 282, as seen through line B-B of FIG. 3. Adhesive 295 is shown in FIG. 4 as being applied in a spiral fashion to the outer lateral edges of the material. It is preferred that adhesive 295 be applied in a spiral manner by techniques known in the art. Those skilled in the art will appreciate, however, that the invention is not limited to spiral application of adhesive 295, and that the adhesive 295 can be applied to upper or lower layer 280, 282, or both, in any known manner using techniques known in the art. It is particularly preferred in the invention to provide a curtain coat of adhesive intermittently to the upper and/or lower layers 280, 282, and not to apply the adhesive in a spiral pattern in the areas where zoning of the SAP is desired.

Figure 5:
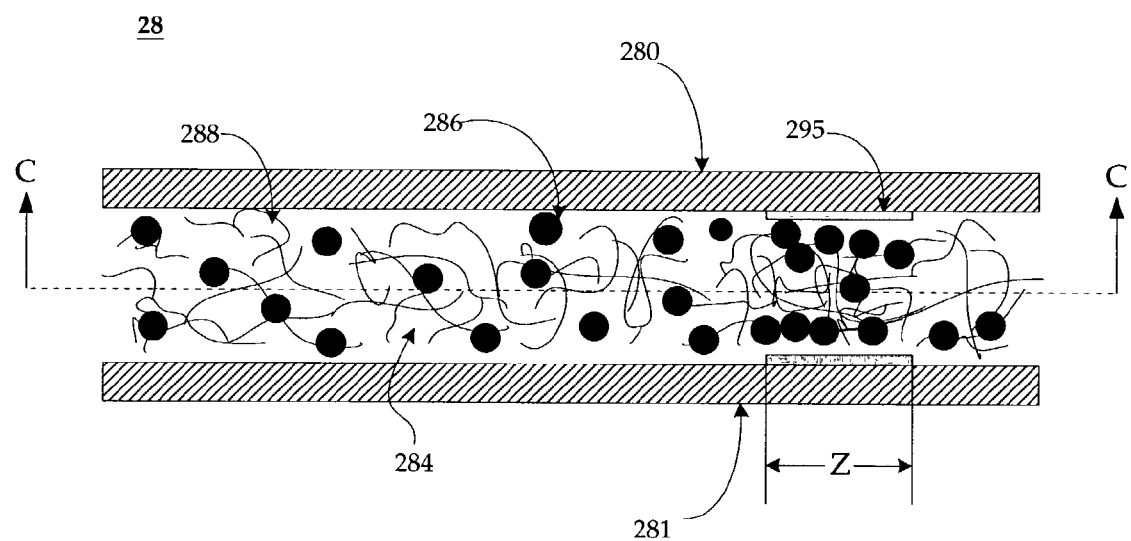
FIG. 5 is a cross-sectional view of an absorbent laminate core in accordance with one embodiment of the invention.
Figure 6:
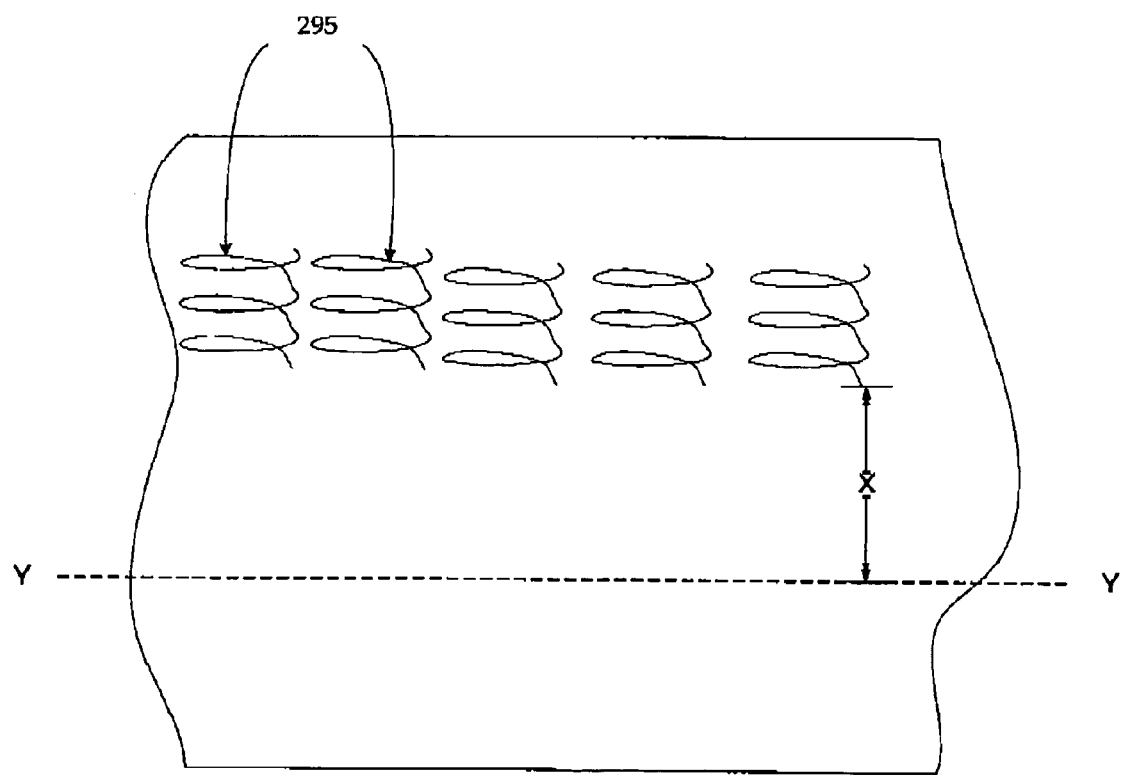
FIG. 6 is a top view of the absorbent laminate core of FIG. 5 taken along line C-C.

FIGS. 5 and 6 illustrate another embodiment of the invention, where adhesive 295 is applied to either the upper or lower layers 280, 282, or both at a distance "X" from the center fold Y-Y thereof (adhesive 295 is shown in FIG. 5 as being applied to both upper layer 280 and lower layer 282, although this is not required in the invention). Applying the adhesive 295 to this particular region of the garment will provide greater zones of absorbency "Z" in specific areas on the absorbent laminate core 28. In FIG. 5, the particular zone of enhanced absorbency Z is near the lateral center of absorbent laminate core 28, but in FIG. 6, it is clear to see that the adhesive is applied at a longitudinal distance "X" from the center fold Y-Y.

In FIG. 6, which is a top view of the absorbent laminate core 28 of FIG. 5 along line C-C, the center fold Y-Y is indicated by the horizontal dotted line. This center fold represents the center fold in the ultimate absorbent garment 10, and not the center of absorbent laminate core 28. Indeed, absorbent laminate core 28 often is disposed in an absorbent garment 10 with more surface area on one side of the center fold than the other. The distance X preferably is from about 6 to about 12 cm when making an absorbent garment for use by male infants, and from about 3 to about 8 cm when making an absorbent garment for use by females.

As shown in FIG. 5, the tow fibers 288 and SAP material 286 are present in a greater amount in the zoned areas Z where adhesive 295 has been applied. While not intending on being bound by any theory, the present inventors believe that the median pore size of the porous matrix of tow fibers is greater than the mean diameter of the SAP particles 286 thereby allowing the SAP particles 286 to migrate until they are affixed in position by compression, or other means known in the art. Thus, the SAP particles 286 are free to move about in absorbent laminate core 28 for a given period of time during manufacture. When the SAP particles 286 encounter adhesive material 295, they will tend to stop migration and remain in place. The same holds true for the individual fibers 288 that make up the porous fibrous matrix of tow fibers. They too will move about for the same given period of time during manufacture, and will tend to stop migration and remain in place at or about the location of the adhesive 295. The greater concentration of tow fibers in these zoned areas "Z" also will tend to fix the SAP material 286 in place.

Figure 7:
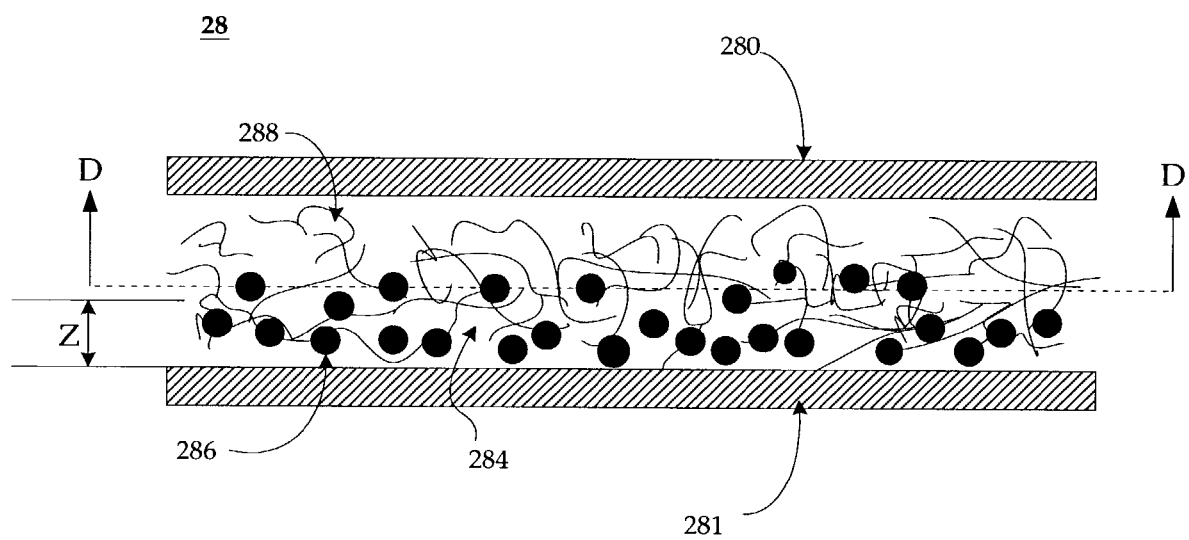
FIG. 7 is a cross-sectional view of an absorbent laminate core in accordance with another embodiment of the invention.

FIG. 7 illustrates another embodiment of the invention whereby no adhesive is applied to either upper or lower layer 280, 282 during manufacture of absorbent laminate core 28. In this embodiment, the SAP material 286 will tend to migrate due to the force of gravity to the lowest portion of the absorbent laminate core 28, due in part to the large median pore size of the porous fiber matrix created by tow fibers 288. Thus, a zoned area of absorbency "Z" is created near the bottom portion of absorbent laminate core 28, and if absorbent laminate core 28 is cupped at all during manufacture, which it may be, then SAP particles 286 will migrate to the lateral center portions of absorbent laminate core 28 as well.

An absorbent laminate core 28 having a zone "Z" of absorbency near the bottom thereof, is beneficial since most liquid tends to migrate to the lowest gravitational part of the core. Thus, by not employing adhesives 295 to either top or bottom layers 280, 282 during manufacture of absorbent laminate core 28, one can provide an increased concentration of SAP material 286 in the areas of the core where it needs it the most.

FIGS. 3-7 represent only a small handful of the possible configurations of absorbent laminate core 28. In addition to other configurations, additional layers may be present in the absorbent laminate core. For example, absorbent laminate core 28 may include an additional layer, and/or an additional layer 29 can be disposed outside absorbent laminate core 28, as shown in FIG. 2. Any additional layer can be used, including any layer selected from a fluid acquisition layer, a distribution layer, an additional fibrous layer optionally containing SAP, a wicking layer, a storage layer, or combinations and fragments of these layers. Such layers may be provided to assist with transferring fluids to the absorbent laminate core 28, handling fluid surges, preventing rewet, containing absorbent material, improving core stability, or for other purposes. For example, a wicking layer 29 having enhanced lateral wicking capabilities may be provided above the absorbent laminate core shown in FIG. 3, which has enhanced absorbency near its lateral edges. Skilled artisans are familiar with the various additional layers that may be included in an absorbent article, and the present invention is not intended on being limited to any particular type of materials used for those layers. Rather, the invention encompasses all types of wicking layers, all types of distribution layers, etc., to the extent that type of layer is utilized.

One element that is useful as an additional layer 29 in the absorbent article 10 of the invention is a fluid acquisition layer. The fluid acquisition layer typically comprises a hydrophilic fibrous material, and serves to quickly collect and temporarily hold discharged body fluid. A portion of discharged fluid may, depending upon the wearer's position, permeate the acquisition layer and be absorbed by the central fibrous layer 284 in the area proximate to the discharge. However, since fluid is frequently discharged in gushes, the central fibrous layer 284 in such area may not absorb the fluid as quickly as it is discharged. Therefore, the fluid acquisition layer hereof also facilitates transport of the fluid from the point of initial fluid contact to other parts of the absorbent laminate core 28. In the context of the present invention, it should be noted that the term "fluid" includes, but is not limited to, liquids, urine, menses, perspiration, and water based body fluids.

The function of the fluid acquisition layer is relatively important. The fluid acquisition layer preferably has sufficient capillary suction to more fully drain the top sheet 24 and yet not exhibit excessive fluid retention to make it difficult for the underlying layer (e.g., central fibrous layer 284) to desorb the acquisition layer. The acquisition layer may be comprised of several different materials including non woven or woven webs of synthetic fibers including polyester, polypropylene, or polyethylene, natural fibers including cotton or cellulose, blends of such fibers, foams, fluff pulp, apertured films, or any equivalent materials or combinations of materials.

Another useful layer for use in the absorbent laminate core 28 or as an additional layer 29 of the absorbent article 10 includes a fluid distribution layer. Fluid distribution layers of the invention can include any combination or all of three basic components: chemically stiffened, twisted, and curled bulking fibers, high surface area fibers, and binder fibers. In a preferred embodiment of the invention, the fluid distribution layer comprises from about 20% to about 80% of the chemically stiffened, twisted, and cured fibers, from about 10% to about 80% of a high surface area fiber, and from 0% to about 50% of a thermoplastic binding means for increasing physical integrity of the web. All percentages herein refer to weight percentages based on total dry web weight. Preferably, the fluid distribution layer will comprise between about 45% and about 60% of chemically stiffened, twisted, and cured fibers, between about 5% and about 15% of a hot melt fibrous binding means, and between about 30% and about 45% high surface area cellulose binding means. More preferably, the fluid distribution layer comprises about 10% thermoplastic binding means, about 45% chemically stiffened, twisted, and cured fibers, and about 45% high surface area fibers.

Chemical additives can also be used as binding means, and are incorporated into the acquisition/distribution layer at levels typically of about 0.2% to about 2.0%, dry web weight basis. The three basic fiber components are described in greater detail in U.S. Pat. No. 5,549,589, the disclosure of which is incorporated by reference herein in its entirety, and in a manner consistent with this disclosure. The fluid distribution layer also may be comprised of non-woven or woven webs of synthetic fibers, natural fibers, foams, carded, thermal bonded materials, and the like.

Another useful layer in the absorbent laminate core 28 or as an additional layer 29 of absorbent garment 10 the invention includes a storage layer. Such storage layers typically have limited transport and wicking capabilities but high storage or retention capacity, and rely upon the central fibrous layer 284 to distribute incoming fluid over a larger area.

Storage layers or members may be of generally conventional design and composition, selected with regard to the particular application. The storage layer or member may be mono-layer or multi-layer, homogeneous or stratified, profiled or uniform, etc. Materials suitable for use in such storage layers may be natural or synthetic in origin, woven, non-woven, fibrous, cellular, or particulate, and may include particles, layers, or regions of absorbent polymeric gelling materials. Other preferred materials include fluff pulp and SAP composites, either air laid or wet laid, and high capacity resilient foam materials. Storage layer may also have any desired size and/or shape as may prove suitable for a particular application, including square, rectangular, oval, elliptical, oblong, etc. They may also take on a three-dimensional shape or may be substantially planar in nature.

Another useful layer in absorbent laminate core 28 or as an additional layer 29 in the absorbent article 10 of the invention is a wicking layer. Wicking layers usually have both fluid acquisition and fluid distribution properties. For example, vertical wicking, which is in general the ability to transport fluids vertically from the top sheet 24 to the absorbent laminate core 28, is related in many respects to fluid acquisition. Horizontal wicking, which is in general the ability to transport fluids along the horizontal 100 and vertical 102 axes of FIG. 1, is related in many respects to fluid distribution.

Any conventional wicking materials can be used for the wicking layer of the invention. High internal phase emulsion (HIPE) foams such as those disclosed in U.S. Pat. No. 5,650,222 can be used, braided materials such as those disclosed in H1,585, and other conventional fibrous and strand materials can be used. The disclosures of U.S. Pat. No. 5,650,222 and H1,585 are incorporated by reference here in their entirety, and in a manner consistent with the present invention.

The wicking layer also may be comprised of two or more sub-layers containing absorbent materials with differing wicking characteristics. Any of the materials discussed in this context can be used for any and all of the wicking layers. In accordance with the embodiment of the invention discussed immediately above, the wicking layer may include a first member that is made of a material that is capable of rapidly transferring, in the z-direction (e.g., orthogonal to the plane formed by horizontal 100 and vertical 102 axes of FIG. 1), body fluid that is delivered to top sheet 24. The first member may be designed to have a dimension narrower than the dimension of the absorbent laminate core 28. In this regard, the sides of the first member preferably are spaced away from the longitudinal sides of the absorbent laminate core 28 so that body fluid is restricted to the area within the periphery of the first member, before it passes down and is absorbed into central fibrous layer 284 (or second member of the wicking layer). This design is believed to enable the body fluid to be combined in the central area of the absorbent laminate core 28 and to be wicked downward so that a greater quantity of the central fibrous layer 284 can be utilized.

A suitable material for use as a first member having high wicking capacity in the z-direction, is a material available from Kimberly-Clark Corporation, in Neenah, Wis. known as PRISM. PRISM is described in U.S. Pat. No. 5,336,552, which is hereby incorporated by reference in its entirety, and in a manner consistent with this disclosure. PRISM generally is a non woven fabric and comprises extruded multi-component polymeric strands including first and second polymeric components arranged in substantially distinctive zones across the cross-section of the multi-component strands and extending continuously along the length of the multi-component strands. Preferably, the strands are continuous filaments which may be formed by spun bonding techniques. The second component of the strands constitutes at least a portion of the peripheral surface of the multi-component strands continuously along the length of the multi-component strands and includes a blend of a polyolefin and an ethylene alkyl acrylate copolymer. Bonds between the multi-component strands may be formed by the application of heat.

More specifically, the first polymeric component of the multi-component strands is present in an amount of from about 20 to about 80 percent by weight of the strands, and the second polymeric component is present in an amount from about 80 to about 20 percent by weight of the strands. Preferably, the first polymeric component of the multi-component strands is present in an amount of from about 40 to about 60 percent by weight of the strands and the second polymeric component is present in an amount from about 60 to about 40 percent by weight of the strands.

The term "strand" as used herein refers to an elongated extrudate formed by passing a polymer through a forming orifice such as a die. Strands include fibers, which are discontinuous strands having a definite length, and filaments, which are continuous strands of material. The non-woven fabric of the present invention may be formed from staple multi-component fibers. Such staple fibers may be carded and bonded to form the non-woven fabric. Preferably, however, the non-woven fabric of the present invention is made with continuous spun bond multi-component filaments which are extruded, drawn and laid on a traveling forming surface.

The types of non-woven materials that may be employed in any of the wicking layers of the invention include powder-bonded-carded webs, infrared bonded carded webs, and through-air-bonded-carded webs. The infrared and through-air bonded carded webs can optionally include a mixture of different fibers, and the fiber lengths within a selected fabric web may be within the range of about 1.0 to 3.0 inch and an average bulk density of about 0.02 g/cc to about 0.06 g/cc.

The first member of wicking layer also may be a nonwoven fibrous web which includes about 75 percent polyester fibers of at least 6 denier, such as PET (polyethylene terephthalate) fibers available from Celanese AG. The polyester fibers have a length ranging from about 1.5 to 2.0 inches in length. The remaining 25 percent of the fibrous web can be composed of bi-component binder fibers of not more than 3 denier, and preferably about 1.5 denier. The bi-component fiber length ranges from about 1.5 to 2 inches. Suitable bi-component fibers are wettable, polyethylene/polypropylene bi-component fiber, available from Chisso, a business having offices located in Osaka, Japan. The bi-component fiber can be a composite, sheath-core type with the polypropylene forming the core and polyethylene forming the sheath of the composite fiber. The polyester fibers and bi-component fibers generally are homogeneously blended together and are not in a layered configuration. The fibers can be formed into a carded web which is thermally bonded, such as by through-air bonding or infrared bonding.

The second member of wicking layer may be positioned vertically below the first member, and it preferably has a higher wicking capacity along the longitudinal 100 and vertical 102 axes of FIG. 1, than the first member. Preferably, the second member has a wicking capacity at least three time greater than the first member. The second member can be equal in width to the first member, but preferably will be wider. It is preferred that the width of the wicking layer in general be the same as or greater than the width of absorbent laminate core 28.

The second member can be a hydrophilic material formed from various types of natural or synthetic fibers including cellulose fibers, surfactant treated meltblown fibers, wood pulp fibers, regenerated cellulose, cotton fibers or a blend of other fibers. Preferably, the second absorbent member is a material described in U.S. Pat. No. 4,100,324, and is generally known as coform. Coform is available from the Kimberly-Clark Corporation located in Neenah, Wis. and is generally a non-woven material having a fabric-like finish and is made up of an airform matrix of thermoplastic polymeric fibers and a multiplicity of individualized wood pulp fibers. The thermoplastic fiber polymers generally have an average diameter of less than 10 microns with the individualized wood pulp fibers dispersed throughout the matrix and serving to space these microfibers from each other. The material is formed by initially utilizing the primary air stream with the meltblown microfibers and the secondary air stream containing wood pulp fibers and merging the two under turbulent conditions to form an integrated air stream along a forming surface. The fiber-like appearance of this material provides a visual appealing absorbent. Also inherent in the coform material is increased resiliency compared to conventional cellulosic absorbents.

Other suitable materials for use as the wicking layer include high-density air laid fluff pulps, high-density wet laid fluff pulp, multi-groove fibers, and mechanically or chemically modified fibers (surface or internally modified).

It is possible in the present invention that the absorbent laminate core 28 be folded as it is disposed between the top sheet 24 and back sheet 26. The absorbent laminate core 28 can be folded in any suitable manner, including any and all of those disclosed in U.S. Pat. No. 6,068,620. Suitable folds include "C" folds, "G" folds, "U" folds, "A" folds, pleats or "W" folds, and the like.

The invention also relates to a method of making an absorbent laminate core, and an absorbent article that includes providing a top sheet material 24 and a back sheet material 26. The method also includes preparing an absorbent laminate core 28 by disposing a central fibrous layer comprising a mixture of tow fibers and SAP between an upper layer 280 and a lower layer 282. The method includes disposing the absorbent laminate core 28 between the top sheet 24 and the back sheet 26. Preparing the absorbent laminate core 28 includes supplying select regions of adhesive 295 to at least one of the upper and lower layers prior to disposing the central fibrous layer 284 there between, to thereby provide an absorbent laminate core 28 having select regions ("Z") of absorbency due to the presence of varying concentrations of SAP. In one embodiment of the invention, no adhesive is applied to the upper or lower layer thereby providing a gravitationally zoned absorbent laminate core.

Figure 8:
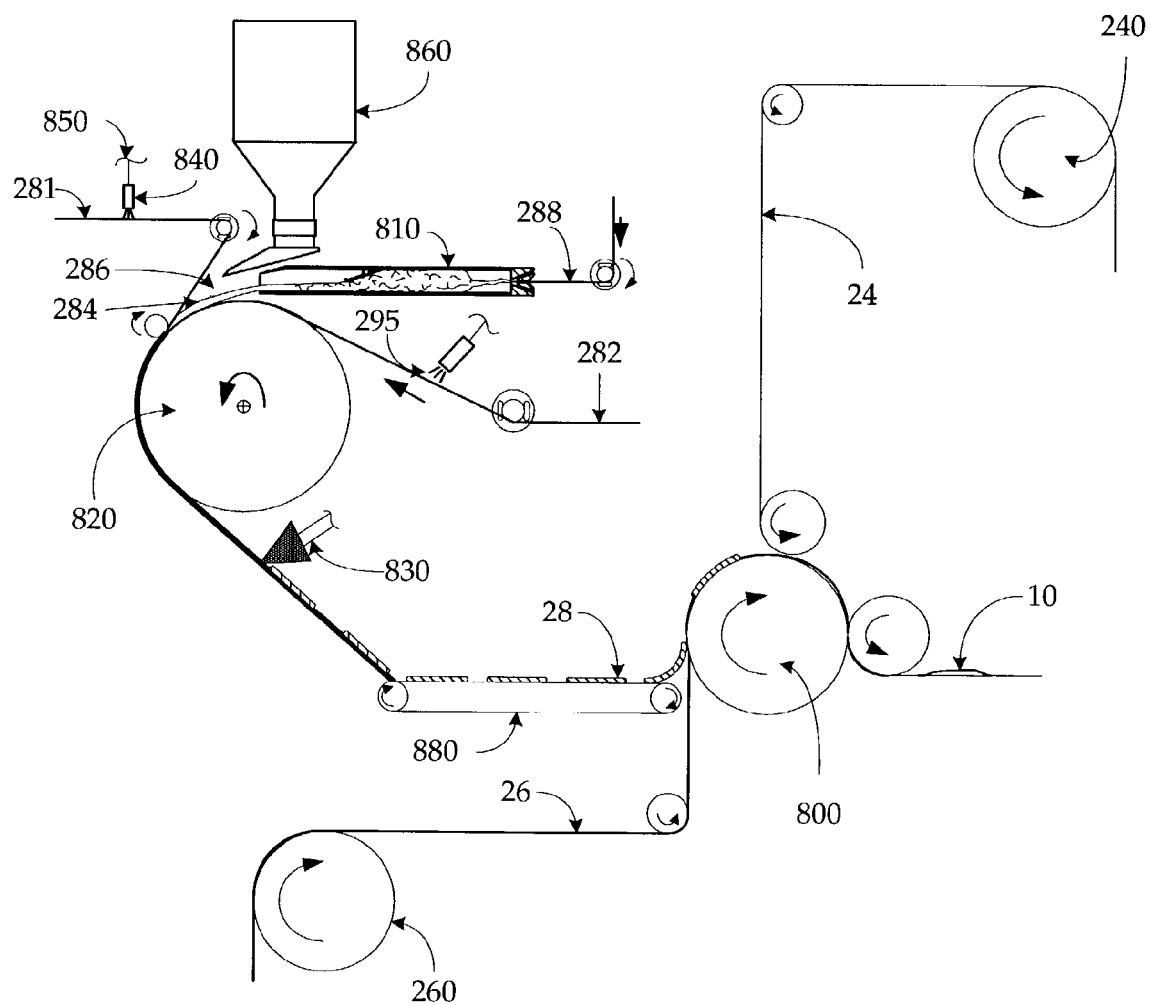
FIG. 8 is an illustration of an apparatus useful in carrying out a method of making an absorbent garment in accordance with the present invention.

FIG. 8 illustrates an apparatus useful in forming an absorbent article 10 in accordance with the present invention. Any type of tow fiber 288 can be supplied to the apparatus and, as conventional in the art, the tow fiber 288 typically is opened prior to forming a fibrous matrix. In this regard, the apparatus includes a tow opener and feeder 810 that is capable of opening any suitable tow material, expanding the tow fiber and feeding the tow fiber to the core forming station 820. Any suitable tow opener and feeder 810 can be used in the method of the invention.

The tow fibers 288 are mixed with superabsorbent polymer (SAP) material 286 to form central fibrous layer 284. The SAP is fed to the core forming station 820 by any SAP feeder 860 capable of feeding the SAP to the core forming station 820. Those skilled in the art are capable of designing a suitable SAP feeder 860 and nozzle configuration to provide adequate mixing of SAP material 286 and tow fibers 288 to form central fibrous layer 284.

Absorbent laminate core 28 can be formed at core forming station 820, where central fibrous layer 284, comprised of SAP material 286 and tow fibers 288, is disposed between an upper layer 281, and a lower layer 282. Upper and lower layers 280, 282 can be fed to core forming unit 820 using any supplying mechanism known in the art, and preferably are fed through one or more feed rollers. Adhesive 295 can be applied to either upper layer 280 or lower layer 282, or both, by an adhesive applicator 840. Again, any mechanism capable of supplying an adhesive, albeit a spray adhesive, or one that is "rubbed" on, can be used in the invention. Suitable adhesives 295 include any adhesive commonly employed in absorbent garments that is useful in adhering one or more tissue and/or non-woven materials together. It is particularly preferred to use construction adhesives, including HL-1258 by H. B. Fuller Company of St. Paul, Minn.; Findley 2031 and H2587-01 by Ato Findley Inc. of Wauwatosa, Wis.; and NS34-5665 by National Starch Co. of Bridgewater, N.J. Other adhesives that may be used in the invention include 34-578A, available from National Starch Co. of Bridgewater, N.J. The adhesives used in the invention may be used in all adhesive applications in the absorbent garment, or only in select applications as a construction adhesive for bonding parts of the garment as the top sheet, back sheet, absorbent core, and additional layer(s).

The positioning and amount of adhesive can be altered either during line down time, or during manufacture of absorbent article 10, by controlling the positioning of adhesive applicator 840 with an adhesive applicator controller 850. Any system can be used as adhesive applicator controller 850 to control the amount, if any, and location of application of the adhesive 295. Those skilled in the art are capable of designing a suitable adhesive application controller 850 to apply select amounts of adhesive 295, in select positions on upper and/or lower layers 280, 282, using the guidelines provided herein.

As the SAP material 286 and tow fibers 288 mix together to form central fibrous layer 284, which in turn is disposed between upper layer 280 and lower layer 282 at core forming station 820, the SAP will preferentially migrate to those regions where adhesive 295 exists. Some of these SAP particles may become affixed in the adhesive 295 when the absorbent laminate core 28 is passed through the one or more nip rollers 821 at the core forming station 820. The absorbent laminate cores 28 then are cut to length by cutting knife 830. Cutting knife 830 can be any suitable cutting device capable of cutting absorbent laminate core 28 of the invention. For example, cutting knife 830 can be comprised of a set of rollers; one being an anvil, and another having a knife attached at one point on the roller, whereby the diameter of the roller is selected to coordinate with the speed at which absorbent laminate cores 28 are formed. The knife roller and anvil roller then can rotate at the same speed as the line speed to cut the absorbent laminate core 28 at select areas to form uniform length cores 28. Skilled artisans are capable of designing a suitable cutting knife 830 given the specifics of each article forming assembly line.

The absorbent laminate cores 28 then are transported to forming station 800 via core conveyor 880. Top sheet material 24 may be supplied to forming station 800 by top sheet supply mechanism 240, which can be any supply mechanism capable of supplying top sheet 24 to forming station 800. Preferably, top sheet material 24 is supplied via a supply roller 240 and select feed or guide rollers. Back sheet material 26 likewise can be supplied to forming station 800 by back sheet supply mechanism 260, which can be any supply mechanism capable of supplying back sheet 26 to forming station 800. Preferably, back sheet material 26 is supplied via a supply roller 260 and select feed or guide rollers. Forming station brings together the respective components of absorbent article 10 by disposing absorbent laminate core 28 between top sheet material 24, and back sheet material 26. The final absorbent article 10 then may be cut and folded to the appropriate size and shape downstream from forming station 800, as indicated by the right-facing arrow in FIG. 8.

Other embodiments, uses, and advantages of the invention will be apparent to those skilled in the art from consideration of the specification and practice of the invention disclosed herein. The specification should be considered exemplary only, and the scope of the invention is accordingly intended to be limited only by the following claims.

What is claimed is:

1. An absorbent article having a longitudinal dimension and a lateral dimension comprising:
    a top sheet;
    a back sheet; and
    an absorbent laminate core disposed at least partially between the top sheet and the back sheet;
    wherein the absorbent laminate core is comprised of:
    an upper layer;
    a lower layer, and
    a central absorbent layer comprising a mixture of tow fibers and SAP disposed between the upper and lower layer,
    an adhesive provided on an inner surface of at least one of said upper and lower layers, wherein said inner surface is disposed adjacent to said central absorbent layer therebetween, said adhesive provided at a predetermined location, said SAP being adhered to said adhesive on said inner surface to create higher concentrations of SAP at said predetermined location,
    wherein the absorbent laminate core contains areas of varying absorbency due to said higher concentrations of SAP at said predetermined location,
    wherein the upper and lower layer are comprised of the same material, and the material is selected from the group consisting of tissue, airlaid fluff pulp, synthetic non-woven material, and mixtures or combinations thereof, and
    wherein the upper layer is fluid pervious, and the lower layer is fluid impervious.

2. The absorbent article of claim 1, whereby the article has a first waist region, a second waist region longitudinally opposed to the first waist region, and a crotch region between the first and second waist regions, the article further comprising at least one fastening element attached to a lateral edge of the first waist region; and
    one or more target devices attached to the article in the second waist region, where at least one fastening element and the one or more target devices are capable of attaching to one another, the one or more target devices being located so that the first waist region and second waist region of the garment may be joined to one another to secure the garment on a wearer.

3. The absorbent article of claim 2, further comprising elastic leg gathers comprising one or more elastic materials disposed adjacent a lateral edge of the crotch region, and standing leg gathers disposed on the top sheet adjacent the lateral edge of the crotch region.

4. The absorbent article of claim 2, wherein the at least one fastening element comprises a hook portion of a hook and loop fastener and the one or more target devices comprise the loop portion of a hook and loop fastener.

5. The absorbent article of claim 2, wherein the at least one fastening element is an adhesive tape and the one or more target devices comprise a tape receiving surface.

6. The absorbent article of claim 2, wherein the at least one fastening element is comprised of a pair of laterally extending tabs disposed on the lateral edges of the first waist region, whereby the laterally extending tabs each include at least one fastening element.

7. The absorbent article of claim 1, wherein at least one additional layer is disposed between the absorbent laminate core and the top sheet.

8. The absorbent article of claim 7, wherein the at least one additional layer is selected from the group consisting of a fluid acquisition layer, a distribution layer, an additional fibrous layer optionally containing SAP, a wicking layer, a storage layer, and combinations and fragments thereof.

9. The absorbent article of claim 1, wherein the absorbent laminate core includes at least one additional layer.

10. The absorbent article of claim 9, wherein the at least one additional layer is selected from the group consisting of a fluid acquisition layer, a distribution layer, an additional fibrous layer optionally containing SAP, a wicking layer, a storage layer, and combinations and fragments thereof.

11. The absorbent article of claim 1, wherein the absorbent laminate core is a multi-layered absorbent core unit including two outer tissue layers and a central fibrous layer that comprises from about 50% to about 95% by weight super absorbent polymer (SAP).

12. The absorbent article of claim 11, wherein the central fibrous layer comprises tow fibers selected from the group consisting of cellulose acetate fibers, rayon fibers, LYOCELL fibers, polyacrylonitrile fibers, cotton fibers and cotton linter fibers.

13. The absorbent article of claim 11, wherein the central fibrous layer further comprises up to 10% by weight fluff wood pulp fibers.

14. The absorbent article of claim 11, wherein the central fibrous layer further comprises particulate additives.

15. The absorbent article of claim 1, wherein the tow is a cellulose ester tow.

16. The absorbent article of claim 15, wherein the tow is a cellulose acetate tow.

17. The absorbent article of claim 1, wherein said predetermined location is only adjacent lateral edges of the laminate core.

18. The absorbent article of claim 1, further comprising a lateral center fold located at the approximate longitudinal center of the garment, wherein said predetermined location comprises a lateral center portion of the absorbent laminate core, and at a longitudinal position approximately 6 to about 12 cm from the center fold of the absorbent article.

19. The absorbent article of claim 1, further comprising a lateral center fold located at the approximate longitudinal center of the garment, wherein said predetermined location comprises a lateral center portion of the absorbent laminate core, and at a longitudinal position approximately 3 to about 8 cm from the center fold of the absorbent article.

20. The absorbent article of claim 1, wherein the tow is chemically modified tow.

21. An absorbent laminate core having a longitudinal dimension and a lateral dimension, the absorbent laminate core comprising:
   an upper layer;
   a lower layer, and
   a central absorbent layer comprising a mixture of tow fibers and SAP disposed between the upper and lower layer,
   an adhesive applied provided on an inner surface of at least one of said upper and lower layers, wherein in said inner surface is disposed adjacent to said central absorbent layer therebetween, said adhesive provided at a predetermined location on said inner surface, said SAP being adhered to said adhesive to create higher concentrations of SAP at said predetermined location, and
   wherein the absorbent laminate core contains areas of varying absorbency due to said higher concentrations of SAP at said predetermined location.

22. An absorbent article having a longitudinal dimension and a lateral dimension comprising:
   a top sheet;
   a back sheet; and
   an absorbent laminate core disposed at least partially between the top sheet and the back sheet;
   wherein the absorbent laminate core is comprised of:
   an upper layer;
   a lower layer, and
   a central absorbent layer comprising a mixture of tow fibers and SAP disposed between the upper and lower layer,
   an adhesive disposed on an inner surface of at least one of said upper and lower layers, wherein said inner surface is disposed adjacent to said central absorbent layer therebetween, said adhesive provided at predetermined locations on said inner surface throughout a lateral cross-section of the laminate core, said SAP being adhered to said adhesive to create higher concentrations of SAP at said predetermined locations, and
   wherein the absorbent laminate core contains areas of varying absorbency due to said higher concentrations of SAP at said predetermined locations throughout the lateral cross-section of the laminate core.

23. The absorbent article of claim 22, wherein said upper and lower layer are comprised of the same material, and the material is selected from the group consisting of tissue, airlaid fluff pulp, synthetic non-woven material, and mixtures or combinations thereof.

24. The absorbent article of claim 22, wherein said upper layer is fluid pervious and said lower layer is fluid impervious.

25. A method of making an absorbent laminate core having predetermined regions of higher concentrations of SAP, said method comprising:
   a. disposing a mixture of fibers and SAP between upper and lower layers;
   b. applying an adhesive at predetermined regions on an inner surface of at least one of said upper and lower layers; and
   c. applying said adhesive prior to disposing said mixture of fibers and SAP between said upper and lower layers, such that SAP is adhered to said adhesive and create higher concentrations of SAP at said predetermined regions.

* * * * *